(12) United States Patent
Wimley et al.

(10) Patent No.: US 8,603,966 B2
(45) Date of Patent: Dec. 10, 2013

(54) AMINO ACID-BASED COMPOUNDS, THEIR METHODS OF USE, AND METHODS OF SCREENING

(75) Inventors: William C. Wimley, Mandeville, LA (US); Jessica R. Marks, Austin, TX (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 13/203,490

(22) PCT Filed: Feb. 27, 2010

(86) PCT No.: PCT/US2010/025697
§ 371 (c)(1),
(2), (4) Date: Apr. 8, 2012

(87) PCT Pub. No.: WO2010/099510
PCT Pub. Date: Sep. 2, 2010

(65) Prior Publication Data
US 2012/0190630 A1 Jul. 26, 2012

Related U.S. Application Data

(60) Provisional application No. 61/208,800, filed on Feb. 27, 2009.

(51) Int. Cl.
*A61K 38/00* (2006.01)
*A61K 38/10* (2006.01)

(52) U.S. Cl.
USPC .......................................... 514/1.1; 514/21.5

(58) Field of Classification Search
None
See application file for complete search history.

(56) References Cited

U.S. PATENT DOCUMENTS

2007/0129305 A1* 6/2007 Divita et al. .................... 514/13

FOREIGN PATENT DOCUMENTS

EP          1797901 A1      6/2007
WO    WO 2004/097017    * 11/2004

OTHER PUBLICATIONS

Rathinakumar et al, Biomolecular Engineering by Combinatorial Design and High-throughput Screening: Small, Soluble Peptides that Permeabilize Membranes, J Am Chem Soc. Jul. 30, 2008; 130(30): 9849-9858.*
Rathinakumer et al, Biomolecular engineering by combinatorial design and high-throughput screening: small, soluble peptides that permeabilize membranes, J Am Chem Soc. Jul. 30, 2008;130(30):9849-58.*
Rathinakumar et al., "Broad-Spectrum Antimicrobial Peptides by Rational Combinatorial Design and High-Throughput Screening: The Importance of Interfacial Activity" J Am Chem Soc (2009) vol. 131, pp. 7609-7617.
Rausch et al., "A high-throughput screen for identifying transmembrane pore-forming peptides" Anal Biochem (2001) vol. 293, pp. 258-263.
Rausch et al., "Rational combinatorial design of pore-forming beta-sheet peptides" Proceedings of the National Academy of Sciences of the United States of America (2005) vol. 102, pp. 10511-10515.
Sengupta et al., "Toroidal pores formed by antimicrobial peptides show significant disorder" Biochimica et Biophysica Acta-Biomembranes (2008), vol. 1778, pp. 2308-2317.
Shai et al., "From 'carpet' mechanism to de-novo designed diastereomeric cell-selective antimicrobial peptides" Peptides (2001) vol. 22, pp. 1629-1641.
Veldhoen et al., "Recent developments in peptide-based nucleic acid delivery" International Journal of Molecular Sciences (2008) vol. 9, pp. 1276-1320.
Walkenhorst et al., "Polar residues in transmembrane helices can decrease electrophoretic mobility in polyacrylamide gels without causing helix dimerization" Biochim Biophys Acta (2009) vol. 1788, pp. 1321-1331.
White et al., "Protein folding in membranes: Determining the energetics of peptide-bilayer interactions" Methods Enzymol (1998) vol. 295, pp. 62-87.
White et al., "Membrane protein folding and stability: Physical principles" Annu Rev Biophys Biomol Struc (1999) vol. 28, pp. 319-365.
White et al., "How membranes shape protein structure" J Biol Chem (2001) vol. 276, No. 35, pp. 32395-32398.
Wiener et al., "Transbilayer distribution of bromine in fluid bilayers containing a specifically brominated analog of dioleoylphosphatidylcholine" Biochemistry (1991) vol. 30, pp. 6997-7008.
Wiener et al., (1992) "Structure of a fluid dioleoylphosphatidylcholine bilayer determined by joint refinement of x-ray and neutron diffraction data. III. Complete structure" Biophys J (1992) vol. 61, pp. 434-447.
Wimley et al., "Solvation energies of amino acid sidechains and backbone in a family of host-guest pentapeptides" Biochemistry (1996a) vol. 35, pp. 5109-5124.
Wimley et al., "Direct measurement of salt-bridge solvation energies using a peptide model system: Implications for protein stability" Proc Natl Acad Sci USA (1996b) vol. 93, pp. 2985-2990.
Wimley et al., "Experimentally determined hydrophobicity scale for proteins at membrane interfaces" Nature Struct Biol (1996c) vol. 3, No. 10, pp. 842-848.

(Continued)

*Primary Examiner* — Cecilia J Tsang
*Assistant Examiner* — Sergio Coffa
(74) *Attorney, Agent, or Firm* — Calfee, Halter & Griswold LLP; Harry J. Guttman

(57) ABSTRACT

Described herein are compounds that comprise amino acids and their pharmaceutical compositions. Methods used to administer the compounds are described. Screening methods including those for determining translocation and leakage are also provided.

35 Claims, 6 Drawing Sheets

(56) References Cited

OTHER PUBLICATIONS

Wimley et al., "Folding of β-sheet membrane proteins: A hydrophobic hexapeptide model" J Mol Biol (1998) vol. 277, pp. 1091-1110.
PCT/US2010/025697, International Search Report, mailed Nov. 18, 2010, 6 pp.
PCT/US2010/025697, Written Opinion, mailed Nov. 18, 2010, 6 pp.
Almeida et al., "Mechanisms of Antimicrobial, Cytolytic, and Cell-Penetrating Peptides: From Kinetics to Thermodynamics" Biochemistry (2009) vol. 48, pp. 8083-8093.
Bechinger, "A dynamic view of peptides and proteins in membranes" Cellular and Molecular Life Sciences (2008) vol. 65, pp. 3028-3039.
Bechinger, "Rationalizing the membrane interactions of cationic amphipathic antimicrobial peptides by their molecular shape" Current Opinion in Colloid & Interface Science (2009) vol. 14, pp. 349-355.
Bechinger et al., "Detergent-like actions of linear amphipathic cationic antimicrobial peptides" Biochimica et Biophysica Acta-Biomembranes (2006) vol. 1758, pp. 1529-1539.
Carter, "Techniques for Conjugation of Synthetic Peptides to Carrier Molecules" from Methods in Molecular Biology, vol. 36 Peptide Analysis Protocols, Edited by Dunn and Pennington (Copyright 1994) Humana Press Inc, Totowa, NJ, pp. 155-191.
Chang et al., "Characterization of antimicrobial peptide activity by electrochemical impedance spectroscopy" Biochim Biophys Acta (2008) vol. 1778, pp. 2430-2436.
Chugh et al., "Study of uptake of cell penetrating peptides and their cargoes in permeabilized wheat immature embryo" FEBS Journal (2008) vol. 275, pp. 2403-2414.
Ghandi et al., "A novel cell-penetrating peptide sequence derived by structural minimization of a snake toxin exhibits preferential nucleolar localization" J. Med. Chem. (2008) vol. 51, pp. 7041-7044.
Gregory et al., "Magainin 2 Revisited: A Test of the Quantitative Model for the All-or-None Permeabilization of Phospholipid Vesicles" Biophys J (2009) vol. 96, pp. 116-131.
Han et al., "Neutron diffraction studies of fluid bilayers with transmembrane proteins: Structural consequences of the achondroplasia mutation" Biophys J (2006) vol. 91, pp. 3736-3747.
Han et al., "Protein folding in membranes: Insights from neutron diffraction studies of a membrane beta-sheet oligomer" Biophys J (2008) vol. 94, pp. 492-505.
Han et al., "Viewing the Bilayer Hydrocarbon Core Using Neutron Diffraction" J Membr Biol (2009) vol. 227, pp. 123-131.
Hancock et al., "Antimicrobial and host-defense peptides as new anti-infective therapeutic strategies" Nature Biotechnology (2006) vol. 24, pp. 1551-1557.
Heitz et al., "Twenty years of cell-penetrating peptides: from molecular mechanisms to therapeutics" British Journal of Pharmacology (2009) vol. 157, pp. 195-206.
Howl et al., "The many futures for cell-penetrating peptides: how soon is now?" Biochem. Soc. Trans. (2007) vol. 34, part 4, pp. 767-769.
Hristova et al., "Interactions of monomeric rabbit neutrophil defensins with bilayers: Comparison with dimeric human defensin HNP-2" Biochemistry (1996) vol. 35, pp. 11888-11894.
Hristova et al., "Determination of the hydrocarbon core structure of fluid dioleoylphosphocholine (DOPC) bilayers by x-ray diffraction using specific bromination of the double-bonds: Effect of hydration" Biophys J (1998) vol. 74, pp. 2419-2433.
Hristova et al., "An amphipathic α-helix at a membrane interface: A structural study using a novel x-ray diffraction method" J Mol Biol (1999) vol. 290, pp. 99-117.
Hristova et al., "Structure, location, and lipid perturbations of melittin at the membrane interface" Biophys J (2001) vol. 80, pp. 801-811.
Hristova et al., "An experiment-based algorithm for predicting the partitioning of unfolded peptides into phosphatidylcholine bilayer interfaces" Biochemistry (2005) vol. 44, pp. 12614-12619.
Jabbari, "Targeted Delivery with Peptidomimetic Conjugated Self-Assembled Nanoparticles" Pharmaceutical Research (2009) vol. 26, No. 3, pp. 612-630.
Jayasinghe et al., "Energetics, stability, and prediction of transmembrane helices" J Mol Biol (2001) vol. 312, pp. 927-934.
Jenssen et al., "Peptide antimicrobial agents" Clinical Microbiology Reviews (2006) vol. 19, No. 3, pp. 491-511.
Jin et al., "Antimicrobial activities and structures of two linear cationic peptide families with various amphipathic beta-sheet and alpha-helical potentials" Antimicrob Agents Chemother (2005) vol. 49, No. 12, pp. 4957-4964.
Kersemans et al., "Cell penetrating peptides for in vivo molecular imaging applications" Current Pharmaceutical Design (2008) vol. 14, pp. 2415-2427.
Kucerka et al., "Structure of fully hydrated fluid phase DMPC and DLPC lipid bilayers using X-ray scattering from oriented multilamellar arrays and from unilamellar vesicles" Biophys J (2005) vol. 88, pp. 2626-2637.
Kucerka et al., "Structure of fully hydrated fluid phase lipid bilayers with monounsaturated chains" J Membr Biol (2006) vol. 208, pp. 193-202.
Li et al., "Imaging FRET Measurements of Transmembrane Helix Interactions in Lipid Bilayers on a Solid Support" Langmuir (2004) vol. 20, pp. 9053-9060.
Li et al., "Quantitative measurements of protein interactions in a crowded cellular environment" Anal Chem (2008) vol. 80, pp. 5976-5985.
Lin et al., "Impedance spectroscopy of bilayer membranes on single crystal silicon" Biointerphases (2008) vol. 3, No. 2, pp. 33-40.
Lin et al., "Electrically addressable, biologically relevant surface-supported bilayers" Langmuir (2010a) vol. 26, No. 14, pp. 12054-12059.
Lin et al., "Effect of a polymer cushion on the electrical properties and stability of surface-supported lipid bilayers" Langmuir (2010b) vol. 26, No. 5, pp. 3544-3548.
Magzoub et al., "Comparison of the interaction, positioning, structure induction and membrane perturbation of cell-penetrating peptides and non-translocating variants with phospholipid vesicles" Biophys Chem (2003) vol. 103, pp. 271-288.
Majkrzak et al., "First-principles determination of hybrid bilayer membrane structure by phase-sensitive neutron reflectometry" Biophys J (2000a) vol. 79, pp. 3330-3340.
Majkrzak et al., "Experimental demonstration of phase determination in neutron reflectometry by variation of the surounding media" Physica B (2000b) vol. 283, pp. 248-252.
Marks et al., "Spontaneous membrane-translocating peptides by orthogonal high-throughput screening" J. Am. Chem. Soc. (2011) vol. 133, pp. 8995-9004. (plus supplemental information).
Marr et al., "Antibacterial peptides for therapeutic use: obstacles and realistic outlook" Current Opinion in Pharmacology (2006) vol. 6, pp. 468-472.
Merzlyakov et al., "Spectral Forster resonance energy transfer detection of protein interactions in surface-supported bilayers" Langmuir (2006a) vol. 22, pp. 6986-6992.
Merzlyakov et al., "Surface-supported bilayers with transmembrane proteins: role of the polymer cushion revisited" Langmuir (2006b) vol. 22, pp. 10145-10151.
Merzlyakov et al., "Directed assembly of surface-supported bilayers with transmembrane helices" Langmuir (2006c) vol. 22, pp. 1247-1253.
Merzlyakov et al., "Transmembrane helix heterodimerization in lipids bilayers: probing the energetics behind autosomal dominant growth disorders" J Mol Biol (2006d) vol. 358, pp. 1-7.
Merzlyakov et al., "Studies of receptor tyrosine kinase transmembrane domain interactions: The EmEx-FRET method" J Membr Biol (2007) vol. 215, pp. 93-103.
Merzlyakov et al., "Surface supported bilayer platform for studies of lateral association of proteins in membranes (Mini Review)" Biointerphases (2008) vol. 3, No. 2, pp. FA80-FA84.
Nikolov et al., "Bias-dependent admittance in hybrid bilayer membranes" Langmuir (2006) vol. 22, pp. 7156-7158.

(56) References Cited

OTHER PUBLICATIONS

Nikolov et al., "Electrical measurements of bilayer membranes formed by Langmuir-Blodgett deposition on single-crystal silicon" Langmuir (2007) vol. 23, pp. 13040-13045.
Oskam et al., "Electrical properties of n-type (111)Si in aqueous K4Fe(CN)(6) solution .1. Interface states and recombination impedance" Journal of the Electrochemical Society (1996a) vol. 143, No. 8, pp. 2531-2537.
Oskam et al., "Electrical properties of n-type (111)Si in aqueous K4Fe(CN)(4) solution .2. Intensity modulated photocurrent spectroscopy" Journal of the Electrochemical Society (1996b) vol. 143, No. 8, pp. 2538-2543.
Rathinakumar et al., "Biomolecular engineering by combinatorial design and high-throughput screening: Small, soluble peptides that permeabilize membranes" J Am Chem Soc (2008) vol. 130, No. 30, pp. 9849-9858.

* cited by examiner

AMINO ACID-BASED COMPOUNDS, THEIR METHODS OF USE, AND METHODS OF SCREENING

CROSS-REFERENCE TO RELATED APPLICATIONS

This application is a National Stage Entry of International Application No. PCT/US2010/025697 filed Feb. 27, 2010, which is incorporated by reference in its entirety, which claims the benefit of U.S. Provisional Application No. 61/208,800, filed Feb. 27, 2009, which is herein incorporated by reference in its entirety.

GOVERNMENT RIGHTS

This invention was made in part with government support under NIGMS60000 awarded by National Institutes of Health. The U.S. Government may have certain rights in the invention.

BACKGROUND

Cell-penetrating peptides (CPPs) can be peptides of less than 30 amino acids that may be able to penetrate cell membranes and translocate different cargo into cells. The mechanism of cell translocation can be receptor and energy independent. Although, in certain cases, translocation can be partially mediated by endocytosis.

The cell membrane can pose a hurdle to the use of pharmacologically active biomacromolecules that are not per se actively translocated into cells. One approach to deliver such molecules involves tethering or complexing them with CPPs that are able to cross the plasma membrane of cells.

SUMMARY

In accordance with some embodiments of the present invention, a compound is selected from Formula (I)

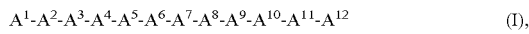  (I), where the $A^1$ to $A^{12}$ are provided herein.

Other embodiment of the present invention include a compound consisting of the compound of Formula (I) linked to a solid support by a solid support linker. Still other embodiments of the present invention include a compound of Formula (II) which consists of the compound of Formula (I) linked to a cargo molecule by a cargo linker. In some instances, Formula (II) can be linked to a solid support by a solid support linker.

Other embodiments include methods for administering at least one compound of Formula (I) comprising administering at least one compound Formula (I) to a cell or liposome.

Still other embodiments include methods for administering at least one compound of Formula (II) comprising administering at least one compound Formula (II) to a cell or liposome.

In some embodiments, methods for administering at least one compound of Formula (I) comprising administering at least one compound Formula (I) to an animal.

In other embodiments, methods for administering at least one compound of Formula (II) comprising administering at least one compound Formula (II) to an animal.

Embodiments also include pharmaceutical compositions comprising at least one compound of Formula (I).

Other embodiments include pharmaceutical compositions comprising at least one compound of Formula (II).

Still other embodiments include methods for screening a molecule for translocation comprising
contacting a screening molecule with a liposome solution comprising an extra-liposome molecule and at least one liposome;
determining leakage from the at least one liposome by determining an amount of a first measurable entity, a rate of formation of a first measurable entity, or both; and
determining crossing the liposomal lipid bilayer of the at least one liposome by the screening molecule by determining an amount of a second measurable entity, a rate of formation of a second measurable entity, or both.

In this screening method, the liposome solution comprises an intra-liposome solution and an extra-liposome solution. Also, the intra-liposome solution comprises a first intra-liposome molecule which, upon leakage, complexes with an extra-liposome molecule to provide the first measureable entity. And the first measurable entity can be in the intra-liposome solution, in the extra-liposome solution, or both. The screening molecule comprises a cleavable moiety which, upon contact with an intra-liposome enzyme or the intra-liposome environment, can cleave the cleavable moiety to provide the second measurable entity.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
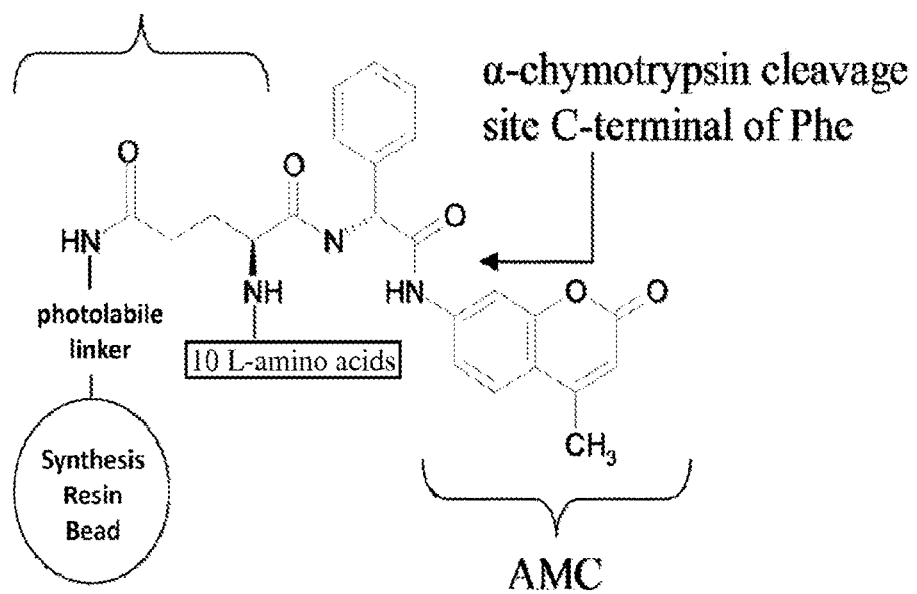
FIG. 1. Some components of the peptides used in the highthroughput translocation assay: the photolabile linker, amidomethylcoumarin (AMC), and a chymotrypsin cleavage site.

Some embodiments of the invention include a compound selected from Formula (I)

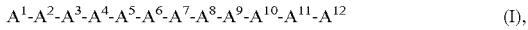  (I), where $A^1$ is selected from the group consisting of L-Arg, D-Arg, L-Pro, and D-Pro;
$A^2$ is selected from the group consisting of L-Arg, D-Arg, L-Lys, D-Lys, L-Leu, and D-Leu;
$A^3$ is selected from the group consisting of L-Arg, D-Arg, L-Lys, D-Lys, L-Ile, D-Ile, and Gly;

$A^4$ is selected from the group consisting of L-Arg, D-Arg, L-Leu, D-Leu, L-Tyr, and D-Tyr;

$A^5$ is selected from the group consisting of L-Arg, D-Arg, L-Pro, D-Pro, L-Leu, and D-Leu;

$A^6$ is selected from the group consisting of L-Arg, D-Arg, L-Phe, D-Phe, L-Gln, and D-Gln;

$A^7$ is selected from the group consisting of L-Arg, D-Arg, L-Lys, D-Lys, L-Pro, D-Pro, L-Leu, and D-Leu;

$A^8$ is selected from the group consisting of L-Arg, D-Arg, L-Leu, and D-Leu;

$A^9$ is selected from the group consisting of L-Arg, D-Arg, L-Leu, and D-Leu;

$A^{10}$ is Gly;

$A^{11}$ is selected from the group consisting of L-Gln and D-Gln; and $A^{12}$ is selected from the group consisting of L-Phe and D-Phe. In some embodiments, all of the chiral amino acids in Formula (I) are L-amino acids. In other embodiments, all of the chiral amino acids in Formula (I) are D-amino acids. In still other embodiments, the number of L-amino acids in Formula (I) is selected from the group consisting of 1, 2, 3, 4, 5, 6, 7, 8, 9, 10, and 11. In some instances, $A^1$, $A^2$, $A^3$, and $A^4$ are all L-amino acids. In other embodiments, $A^1$, $A^2$, $A^3$, and $A^4$ are all D-amino acids. In some embodiments, 1, 2, or 3 of $A^1$, $A^2$, $A^3$, and $A^4$ are L-amino acids. In other embodiments, $A^5$, $A^6$, $A^7$, $A^8$, and $A^9$ are all L-amino acids. In some instances, $A^5$, $A^6$, $A^7$, $A^8$, and $A^9$ are all D-amino acids. In other instances, 1, 2, 3, or 4 of $A^1$, $A^5$, $A^6$, $A^7$, $A^8$, and $A^9$ are L-amino acids. In some embodiments, $A^{10}$, $A^{11}$ and $A^{12}$ are all L-amino acids. In some instances, $A^{10}$, $A^{11}$, and $A^{12}$ are all D-amino acids. In some instances, 1 or 2 of $A^{10}$, $A^{11}$, and $A^{12}$ are L-amino acids.

In some embodiments, $A^1$ is selected from the group consisting of L-Pro and D-Pro;

$A^2$ is selected from the group consisting of L-Leu and D-Leu;

$A^3$ is selected from the group consisting of L-Ile, D-Ile, and Gly; and $A^4$ is selected from the group consisting of L-Leu, D-Leu, L-Tyr, and D-Tyr. In some instances, $A^1$, $A^2$, $A^3$, and $A^4$ are all L-amino acids. In some instances, $A^1$, $A^2$, $A^3$, and $A^4$ are all D-amino acids. In some instances, 1, 2, or 3 of $A^1$, $A^2$, $A^3$, and $A^4$ are L-amino acids.

In some embodiments, $A^5$ is selected from the group consisting of L-Leu and D-Leu;

$A^6$ is selected from the group consisting of L-Arg and D-Arg;

$A^7$ is selected from the group consisting of L-Leu and D-Leu;

$A^8$ is selected from the group consisting of L-Leu and D-Leu; and $A^9$ is selected from the group consisting of L-Arg and D-Arg. In some instances, $A^5$, $A^6$, $A^7$, $A^8$, and $A^9$ are all L-amino acids. In other embodiments, $A^5$, $A^6$, $A^7$, $A^8$, and $A^9$ are all D-amino acids. In some instances, 1, 2, 3, or 4 of $A^5$, $A^6$, $A^7$, $A^8$, and $A^9$ are L-amino acids.

In some embodiments, $A^1$ is selected from the group consisting of L-Pro and D-Pro;

$A^2$ is selected from the group consisting of L-Leu and D-Leu;

$A^3$ is selected from the group consisting of L-Ile, D-Ile, and Gly;

$A^4$ is selected from the group consisting of L-Leu, D-Leu, L-Tyr, and D-Tyr;

$A^5$ is selected from the group consisting of L-Leu and D-Leu;

$A^6$ is selected from the group consisting of L-Arg and D-Arg;

$A^7$ is selected from the group consisting of L-Leu and D-Leu;

$A^8$ is selected from the group consisting of L-Leu and D-Leu; and $A^9$ is selected from the group consisting of L-Arg and D-Arg. In some embodiments, $A^1$, $A^2$, $A^3$, $A^4$, $A^5$, $A^6$, $A^7$, $A^8$, and $A^9$ are L-amino acids. In other embodiments, $A^1$, $A^2$, $A^3$, $A^4$, $A^5$, $A^6$, $A^7$, $A^8$, and $A^9$ are all D-amino acids. In still other embodiments, 1, 2, 3, 4, 5, 6, 7, or 8 of $A^1$, $A^2$, $A^3$, $A^4$, $A^5$, $A^6$, $A^7$, $A^8$, and $A^9$ are L-amino acids. In some instances, $A^1$, $A^2$, $A^3$, and $A^4$ are all L-amino acids. In some instances, $A^1$, $A^2$, $A^3$, and $A^4$ are all D-amino acids. In other instances, 1, 2, or 3 of $A^1$, $A^2$, $A^3$, and $A^4$ are L-amino acids. In some embodiments, $A^5$, $A^6$, $A^7$, $A^8$, and $A^9$ are all L-amino acids. In other embodiments, $A^5$, $A^6$, $A^7$, $A^8$, and $A^9$ are all D-amino acids. In some instances, 1, 2, 3, or 4 of $A^5$, $A^6$, $A^7$, $A^8$, and $A^9$ are L-amino acids.

In some embodiments, Formula (I) is designed to be degraded, such that, for example, the amino acid sequence will be cleaved at one or more points by a change in solution conditions or by one or more enzymes, such as proteases. Some examples of proteases include, serine proteases (such as, but not limited to, chymotrypsin, trypsin, elastase, and subtilisin), threonine proteases, cysteine proteases (such as, but not limited to, actinidain, bromelain, calpains, caspases, cathepsins, mir1-CP, and papain), aspartate proteases (such as, but not limited to, HIV-1 protease, chymosin, cathepsin D, pepsin, and plasmepsin), metalloproteases (such as but not limited to, metalloexopeptidases and metalloendopeptidases), and glutamic acid proteases.

In other embodiments, Formula (I) is designed to prevent degradation, as for example, by cleavage. Cleavage can, for example, be due to a change in solution conditions or by an enzyme, such as, but not limited to, those enzymes mentioned in the discussion of degradation. Such degradation-prevention designs can include a design that prevents recognition of one or more cleavage sites by one or more enzymes, including but not limited to, the choice of sequence of L-amino acids or the choice of one or more D-amino acids.

In some embodiments, the compound of Formula (I) has a net charge (i.e., including the amino terminus charge) of +2, +3, +4, +5, +6, +7, +8, +9, or +10.

In some embodiments, a compound of Formula (I) can be selected from the following sequences that include only L-amino acids for the chiral amino acids:

```
                                     (SEQ ID NO: 1)
Arg-Leu-Ile-Tyr-Leu-Arg-Leu-Leu-Arg-Gly-Gln-Phe;

(SEQ ID NO: 2)
Arg-Lys-Ile-Leu-Leu-Arg-Leu-Leu-Arg-Gly-Gln-Phe;

(SEQ ID NO: 3)
Pro-Leu-Ile-Leu-Leu-Arg-Leu-Leu-Arg-Gly-Gln-Phe;

(SEQ ID NO: 4)
Pro-Leu-Ile-Tyr-Leu-Arg-Leu-Leu-Arg-Gly-Gln-Phe;

(SEQ ID NO: 5)
Pro-Leu-Gly-Tyr-Leu-Phe-Leu-Leu-Arg-Gly-Gln-Phe;

(SEQ ID NO: 6)
Arg-Leu-Ile-Leu-Leu-Phe-Arg-Arg-Leu-Gly-Gln-Phe;

(SEQ ID NO: 7)
Pro-Leu-Arg-Leu-Arg-Phe-Leu-Leu-Arg-Gly-Gln-Phe;
```

Arg-Leu-Ile-Arg-Leu-Phe-Leu-Leu-Arg-Gly-Gln-Phe;  (SEQ ID NO: 8)

Pro-Leu-Ile-Tyr-Pro-Phe-Leu-Arg-Leu-Gly-Gln-Phe;  (SEQ ID NO: 9)

Arg-Arg-Ile-Leu-Leu-Gln-Leu-Leu-Arg-Gly-Gln-Phe;  (SEQ ID NO: 10)

Pro-Leu-Arg-Leu-Leu-Arg-Leu-Leu-Arg-Gly-Gln-Phe;  (SEQ ID NO: 11)

Pro-Lys-Ile-Leu-Leu-Phe-Lys-Leu-Leu-Gly-Gln-Phe;  (SEQ ID NO: 12)

Pro-Arg-Lys-Leu-Leu-Gln-Leu-Leu-Leu-Gly-Gln-Phe;  (SEQ ID NO: 13)

Pro-Arg-Ile-Tyr-Leu-Arg-Leu-Leu-Leu-Gly-Gln-Phe;  (SEQ ID NO: 14)

Arg-Arg-Ile-Leu-Leu-Gln-Leu-Leu-Leu-Gly-Gln-Phe;  (SEQ ID NO: 15)

Pro-Arg-Ile-Leu-Leu-Arg-Leu-Leu-Leu-Gly-Gln-Phe;  (SEQ ID NO: 16)

Arg-Leu-Ile-Leu-Arg-Gln-Leu-Leu-Arg-Gly-Gln-Phe;  (SEQ ID NO: 17)

Arg-Lys-Gly-Leu-Leu-Gln-Leu-Leu-Leu-Gly-Gln-Phe;  (SEQ ID NO: 18)

Arg-Leu-Ile-Arg-Gln-Leu-Leu-Leu-Gly-Gln-Phe;  (SEQ ID NO: 19)

Pro-Lys-Gln-Leu-Leu-Arg-Leu-Leu-Leu-Gly-Gln-Phe; and  (SEQ ID NO: 20)

Arg-Lys-Arg-Leu-Leu-Gln-Leu-Leu-Leu-Gly-Gln-Phe.  (SEQ ID NO: 21)

In other embodiments, a compound of Formula (I) can be selected from the following sequences that include only D-amino acids for the chiral amino acids:

Arg-Leu-Ile-Tyr-Leu-Arg-Leu-Leu-Arg-Gly-Gln-Phe;

Arg-Lys-Ile-Leu-Leu-Arg-Leu-Leu-Arg-Gly-Gln-Phe;

Pro-Leu-Ile-Leu-Leu-Arg-Leu-Leu-Arg-Gly-Gln-Phe;

Pro-Leu-Ile-Tyr-Leu-Arg-Leu-Leu-Arg-Gly-Gln-Phe;

Pro-Leu-Gly-Tyr-Leu-Phe-Leu-Leu-Arg-Gly-Gln-Phe;

Arg-Leu-Ile-Leu-Leu-Phe-Arg-Arg-Leu-Gly-Gln-Phe;

Pro-Leu-Arg-Leu-Arg-Phe-Leu-Leu-Arg-Gly-Gln-Phe;

Arg-Leu-Ile-Arg-Leu-Phe-Leu-Leu-Arg-Gly-Gln-Phe;

Pro-Leu-Ile-Tyr-Pro-Phe-Leu-Arg-Leu-Gly-Gln-Phe;

Arg-Arg-Ile-Leu-Leu-Gln-Leu-Leu-Arg-Gly-Gln-Phe;

Pro-Leu-Arg-Leu-Leu-Arg-Leu-Leu-Arg-Gly-Gln-Phe;

Pro-Lys-Ile-Leu-Leu-Phe-Lys-Leu-Leu-Gly-Gln-Phe;

Pro-Arg-Lys-Leu-Leu-Gln-Leu-Leu-Leu-Gly-Gln-Phe;

Pro-Arg-Ile-Tyr-Leu-Arg-Leu-Leu-Leu-Gly-Gln-Phe;

Arg-Arg-Ile-Leu-Leu-Gln-Leu-Leu-Leu-Gly-Gln-Phe;

Pro-Arg-Ile-Leu-Leu-Arg-Leu-Leu-Leu-Gly-Gln-Phe;

Arg-Leu-Ile-Leu-Arg-Gln-Leu-Leu-Arg-Gly-Gln-Phe;

Arg-Lys-Gly-Leu-Leu-Gln-Leu-Leu-Leu-Gly-Gln-Phe;

Arg-Leu-Ile-Arg-Gln-Leu-Leu-Gly-Gln-Phe;

Pro-Lys-Gln-Leu-Leu-Arg-Leu-Leu-Leu-Gly-Gln-Phe; and

Arg-Lys-Arg-Leu-Leu-Gln-Leu-Leu-Leu-Gly-Gln-Phe.

In some embodiments, Formula (I) includes one or more of the following L-amino-acid sequences:

Arg-Lys-Lys-Arg-Arg-Gln-Arg-Arg-Gly-Gln-Phe  (SEQ ID NO: 22)
and

Arg-Arg-Arg-Arg-Arg-Arg-Arg-Arg-Gly-Gln-Phe.  (SEQ ID NO: 23)

In some instances, one or both of SEQ ID NOs: 22-23 are excluded from Formula (I). In some instances, Formula (I) comprises the following sequence:

Arg-Arg-Ile-Arg-Pro-Arg-Pro.  (SEQ ID NO:24)

In some instances, one or more of the amino acid sequences that include SEQ ID NO: 24 are excluded from Formula (I).

In some embodiments, the sum of the number of L-prolines plus D-prolines in Formula (I) is 0, 1, 2, or 3. In other embodiments, the number of L-prolines in Formula (I) is 0, 1, 2, or 3. In still other embodiments, the number of D-prolines in Formula (I) is 0, 1, 2, or 3.

In some embodiments, the sum of L-Pro, D-Pro, Gly, L-Leu, D-Leu, L-Ile, and D-Ile at $A^2$, $A^3$, $A^5$ and $A^7$ is 0, 1, 2, or 3. In other embodiments, the sum of L-Pro, Gly, L-Leu, and L-Ile at $A^2$, $A^3$, $A^5$ and $A^7$ is 0, 1, 2, or 3. In some embodiments, the sum of D-Pro, Gly, D-Leu, and D-Ile at $A^2$, $A^3$, $A^5$ and $A^7$ is 0, 1, 2, or 3. In some embodiments, the sum of L-Pro, D-Pro, L-Leu, D-Leu, L-Ile, D-Ile, L-Tyr, and D-Tyr at $A^4$, $A^5$, $A^7$ and $A^8$ is 0, 1, 2, 3, or 4. In some instances, the sum of L-Pro, L-Leu, L-Ile, and L-Tyr at $A^4$, $A^5$, $A^7$ and $A^8$ is 0, 1, 2, 3, or 4. In other instances, the sum of D-Pro, D-Leu, D-Ile, and D-Tyr at $A^4$, $A^5$, $A^7$ and $A^8$ is 0, 1, 2, 3, or 4.

In some embodiments, $A^7$ is L-Leu or D-Leu; $A^8$ is L-Leu or D-Leu; and $A^9$ is L-Arg or D-Arg. In other embodiments, $A^7$ is L-Leu or D-Leu; $A^8$ is L-Leu or D-Leu; and $A^9$ is L-Leu or D-Leu.

In some embodiments, in Formula (I), the sum of D-Lys plus L-Lys is greater than the sum of D-Arg plus L-Arg. In other embodiments, in Formula (I), the sum of D-Lys plus L-Lys is less than the sum of D-Arg plus L-Arg. In still other embodiments, in Formula (I), the sum of D-Lys plus L-Lys is equal to the sum of D-Arg plus L-Arg.

In some embodiments of the present invention, the compound of Formula (I) is linked to a solid support by a solid support linker. The solid support can be, but is not limited to, beads or resins including those used for solid-phase peptide synthesis (e.g., polystyrene beads, polystyrene resins, polyamide beads, polyamide resins, resins using polyethylene glycol, or beads using polyethylene glycol). Solid support linkers can be, but are not limited to, a bond or photolabile linkers, such as those used in solid phase peptide synthesis (e.g., the Fmoc method or the t-Boc method).

In some embodiments, compounds of Formula (I) can pass through a lipid bilayer (e.g., a cell membrane or a liposome) by, for example, translocation or by leakage (e.g., by creating a pore). In some instances, translocation can occur with minimal toxicity. In still other embodiments, compounds of Formula (I) can cross the lipid bilayer using one or more energy independent pathways, such as, but not limited to translocation, leakage (e.g., pore-formation), and endocytosis. In some embodiments, a compound of Formula (I) can be toxic to microbes (e.g., bacteria or yeast). In some instances, a compound of Formula (I) can be toxic to a microbe at any suitable peptide concentration such as, for example, about 0.1 µM, about 0.5 µM, about 1.0 µM, about 2.5 µM, about 5.0 µM, about 7.5 µM, about, 10 µM, or about 15 µM. In some instances, a compound of Formula (I) can be toxic to a microbe at any suitable peptide to lipid ratio such as, for example, about 1:3000; about 1:1000, about 1:750, about 1:500, about 1:300, or about 1:100.

In some embodiments, a compound of Formula (I) can produce leakage from a liposome, relative to a complete solubilization of the liposome, of at least about 25%, at least about 40%, at least about 60%, at least about 80%, at least about 90%, no more than about 100%, no more than about 99%, no more than about 95%, no more than about 90%, no more than about 80%, or no more than about 20%. In other embodiments, compounds of Formula (I) can translocate into a liposome at a relative rate (e.g., where the rate is relative to the screening molecule exposed to a solution that (a) does not comprise the inhibitor, (b) does not comprise liposomes, and (c) comprises a concentration of intra-liposome enzyme that is equal to the concentration of the intra-liposome enzyme in the liposome solution) of at least about 1.25, at least about 1.5, at least about 2.0, at least about 2.5, no more than about 3.5, no more than about 3.0, no more than about 2.5, no more than about 2.0, or nor more than about 1.0.

Some embodiments of the present invention include syntheses of compounds of Formula (I). Synthesis of a compound of Formula (I) can be performed using any known or available method, including liquid phase synthesis or solid phase synthesis. Solid phase synthesis can be performed using any known or available method, including but not limited to t-Boc synthetic schemes or Fmoc synthetic schemes. For solid phase synthesis, beads or resins can be used as the solid phase, including, but not limited to, polystyrene beads, polystyrene resins, polyamide beads, polyamide resins, resins using polyethylene glycol, and beads using polyethylene glycol.

Some embodiments of the present invention include compounds of Formula (II), which are defined as a compound selected from Formula (I) linked to a cargo molecule by a cargo linker. The cargo molecule can be linked, for example, to the N-terminus of Formula (I), the C-terminus of Formula (I), or a side chain of an amino acid of Formula (I).

In Formula (II), Formula (I) can include any of the embodiments described herein. The cargo linker in Formula (II) can be, but is not limited to, a covalent bond, a D-cysteine, an L-cysteine, an alkylated L-cysteine, an alkylated D-cysteine, two cysteines (which can be D-, L-, or both) connected by a disulfide bond or by a peptide bond, one alkylated cysteine (which can be D- or L-) connected by a peptide bond to a cysteine (which can be D- or L-), two alkylated cysteines (which can be D-, L-, or both) connected by a peptide bond, or an amino acid sequence that is cleavable by a enzyme, such as a protease or an esterase. An alkylated cysteine is a cysteine with the thiol group (-SH) replaced by —S-alkyl, where alkyl can be a $C_1$-$C_6$ alkyl and includes all isomers of the alkyl group. In some embodiments, the cargo linker is designed to be cleaved when the Formula (II) compound proceeds from one environment to another environment, such as, but not limited to, when Formula (II) proceeds (a) from an extracellular solution environment to an intracellular solution environment, (b) from an outside an organelle to inside an organelle (such as, but not limited to, nuclei, mitochondria, chloroplasts, lysosomes, peroxisomes, or vacuoles), or (c) from an extra-liposomal environment to an intra-liposomal environment. The cell for (a) and (b) can be, for example, a prokaryotic cell (e.g., a microbial cell, a gram negative bacteria, or a gram positive bacteria), a plant cell (in vitro or in vivo), or an animal cell (in vitro or in vivo). The cell can be a unicellular organism, or can be obtained from a multicellular organism, e.g., isolated cells from a multicellular host. These can include eukaryotics and prokaryotics, such as strains of *E. coli, Pseudomonas, Bacillus, Streptomyces*, fungi, yeast, insect cells such as *Spodoptera frugiperda* (SF9), animal cells such as CHO and mouse cells, African green monkey cells such as COS 1, COS 7, BSC 1, BSC 40, and BMT 10, and human cells (e.g., cells associated with the blood-brain barrier), as well as plant cells. Of course, the liposomes of (c) can be designed to reflect a certain cell or organelle type by, for example, adjusting the size of the liposome and the lipid composition of the liposome bilayer.

As used herein, "cleave" refers to the removal of a bond by, for example, enzyme action or a change in the solution environment, such as, but not limited to, a change in oxidation state (e.g., reduction or oxidation), change in pH, change ion concentration, or a change in ionic strength.

The "cargo molecule" can be, but is not limited to a dye molecule (such as amidomethylcoumarin ("AMC"), Tetramethyl-6-Carboxyrhodamine ("TAMRA"), and Tetramethyl-5-Carboxyrhodamine), a nanoparticle, a DNA molecule, an RNA molecule, a polypeptide, a drug, or a prodrug. Embodiments of drugs as cargo molecules include, but are not limited to, any polar compound with useful pharmacological properties, but which do not readily translocate across membranes. Embodiments of polypeptides as cargo molecules include, but are not limited to, fluorescent polypeptides (such as green fluorescent protein or its variants), polypeptides that are defective or deficient in genetic diseases (for example, the GM2 activator protein of Tay-Sachs disease), polypeptides related to cell signaling, or polypeptides related to cell death (for example, proapoptotic factor BID). Embodiments of RNA as cargo molecules include, but are not limited to, small interfering RNAs (siRNA) targeting specific messenger RNA (mRNA) for downregulation. Embodiments of DNA as cargo molecules include, but are not limited to, small gene segments for transfection or segments designed to interfere with DNA replication (e.g., replication of viral DNA). Embodiments of nanoparticles as cargo molecules include, but are not limited to, quantum dots (e.g., for imaging or tracking), or nanometallic particles, such as those made of silver or gold. In some embodiments, the cargo molecule is a molecule that normally would not pass through a lipid bilayer, such as, but not limited to, polar molecules (e.g., TAMRA). In some embodiments, the molecular weight of the cargo molecule is at least about 50, at least about 100, at least about 150, no more than about 150, no more than about 300, no more than about 1,000, no more than about 5,000, no more than about 10,000, no more than about 25,000, no more than about 50,000, no more than about 100,000, no more than about 150,000, or no more than about 200,000.

The term "prodrug" as used herein includes compound forms which are transformed in vivo to the corresponding drug, for example, by hydrolysis. Prodrugs are compounds bearing groups which are modified by biotransformation prior to exhibiting their pharmacological action. Such groups include moieties which can be cyclised or cleaved, which compound after biotransformation remains or becomes pharmacologically active. For example, metabolically cleavable groups form a class of groups such as, but not limited to, alkanoyl (e.g., acetyl, propionyl, and butyryl), unsubstituted and substituted carbocyclic aroyl (such as, benzoyl, substituted benzoyl, and 1- and 2-naphthoyl), alkoxycarbonyl (such as ethoxycarbonyl), trialkylsilyl (such as trimethyl- and triethylsilyl), monoesters formed with dicarboxylic acids (such as succinyl), phosphate, sulfate, sulfonate, sulfonyl, sulfinyl.

In some embodiments of the present invention, the compound of Formula (II) is linked to a solid support by a solid support linker. The solid support can be, but is not limited to, beads or resins including those used for solid-phase peptide synthesis (e.g., polystyrene beads, polystyrene resins, polyamide beads, polyamide resins, resins using polyethylene glycol, or beads using polyethylene glycol). Solid support linkers can be, but are not limited to, a covalent bond or photolabile linkers, such as those used in solid phase peptide synthesis (e.g., the Fmoc method or the t-Boc method).

In some embodiments, the compound of Formula (II) can pass through a lipid bilayer (e.g., a cell membrane or a liposome) by, for example, translocation or leakage (e.g., by creating a pore). In some instances, translocation can occur with minimal toxicity. In still other embodiments, the compound of Formula (II) can cross the lipid bilayer using one or more energy independent pathways, such as, but not limited to translocation, leakage (e.g., pore-formation), and endocytosis. In some embodiments, a compound of Formula (II) can be toxic to microbes (e.g., bacteria or yeast). In some instances, a compound of Formula (II) can be toxic to a microbe at any suitable peptide concentration such as about 0.1 µM, about 0.5 µM, about 1.0 µM, about 2.5 µM, about 5.0 µM, about 7.5 µM, about, 10 µM, or about 15 µM. In some instances, a compound of Formula (II) can be toxic to a microbe at any suitable peptide to lipid ratio, such as, for example, about 1:3000; about 1:1000, about 1:750, about 1:500, about 1:300, or about 1:100.

In some embodiments, a compound of Formula (II) can produce leakage from a liposome, relative to a complete solubilization of the liposome, of at least about 25%, at least about 40%, at least about 60%, at least about 80%, at least about 90%, no more than about 100%, no more than about 99%, no more than about 95%, no more than about 90%, no more than about 80%, or no more than about 20%. In some embodiments, compounds of Formula (II) can translocate into a liposome at a relative rate (e.g., where the rate is relative to the screening molecule exposed to a solution that (a) does not comprise the inhibitor, (b) does not comprise liposomes, and (c) comprises a concentration of intra-liposome enzyme that is equal to the concentration of the intra-liposome enzyme in the liposome solution) of at least about 1.25, at least about 1.5, at least about 2.0, at least about 2.5, no more than about 3.5, no more than about 3.0, no more than about 2.5, no more than about 2.0, or nor more than about 1.0.

Some embodiments of the present invention include syntheses of compounds of Formula (II). Synthesis of compounds of Formula (II) can be performed using any known or available method, including liquid phase synthesis, solid phase synthesis or both. Solid phase synthesis can be performed using any known or available method, including but not limited to t-BOC synthetic schemes or Fmoc synthetic schemes. For solid phase synthesis, beads or resins can be used as the solid phase, including, but not limited to, polystyrene beads, polystyrene resins, polyamide beads, polyamide resins, resins using polyethylene glycol, and beads using polyethylene glycol. Any known or available method can be used to attach the cargo linker and cargo molecule for the compounds of Formula (II) including, but not limited to, the methods discussed or referenced in "Techniques for Conjugation of Synthetic Peptides to Carrier Molecules." Mark Carter in Peptide Analysis Protocols. Series: Methods in Molecular Biology, Springer, Volume: 36, Pub. Date: Nov. 7, 1994, Pages 155-191.

Some embodiments of the invention include administration of at least one compound of Formula (I) or Formula (II) to a cell or a liposome. The cell can be a unicellular organism, or can be obtained from a multicellular organism, e.g., isolated cells from a multicellular host. The cell can include eukaryotics and prokaryotics, such as strains of *E. coli, Pseudomonas, Bacillus, Streptomyces,* fungi, yeast, insect cells such as *Spodoptera frugiperda* (SF9), animal cells such as CHO and mouse cells, African green monkey cells such as COS 1, COS 7, BSC 1, BSC 40, and BMT 10, and human cells (e.g., cell associated with the blood brain barrier), as well as plant cells.

Some embodiments of the invention include administration of at least one compound of Formula (I) and Formula (II) to animals by any number of administration routes or formulations. The compounds can also be used to treat animals for a variety of diseases. Animals include but are not limited to canine, bovine, porcine, avian, mammalian, and human.

The route of administration of the compounds may be of any suitable route such as that which provides a concentration in the blood corresponding to a therapeutic concentration. Administration routes that can be used, but are not limited to the oral route, the parenteral route, the cutaneous route, the nasal route, the rectal route, the vaginal route and the ocular route. The choice of administration route can depend on the compound identity, such as the physical and chemical properties of the compound, as well as the age and weight of the animal, the particular disease, and the severity of the disease. Of course, combinations of administration routes can be administered, as desired.

One or more compounds of Formula (I) and Formula (II) can be part of a composition and can be in an amount (by weight of the total composition) of at least about 0.001%, at least about 1%, at least about 10%, at least about 25%, at least about 50%, no more than about 75%, no more than about 90%, no more than about 95%, no more than about 99% or no more than about 99.99%.

One or more compounds of Formula (I) and Formula (II) can purified or isolated in an amount (by weight of the total composition) of at least about 0.001%, at least about 1%, at least about 10%, at least about 25%, at least about 50%, no more than about 75%, no more than about 90%, no more than about 95%, no more than about 99% or no more than about 99.99%.

One or more compounds of Formula (I) and Formula (II) can be part of a pharmaceutical composition and can be in an amount from about 1% to about 99% by weight of the total composition (or from about 10% to about 90%, or from about 25% to about 75%). The composition can be presented in a dosage form which is suitable for the oral, parenteral, rectal, cutaneous, nasal, vaginal, or ocular administration route. The composition can be of the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols, or other suitable forms.

Pharmaceutical compositions can be formulated to release the active compound substantially immediately upon the administration or any substantially predetermined time or times after administration. Such formulations can include, for example, controlled release formulations such as various controlled release compositions and coatings.

Other formulations include those incorporating the drug (or control release formulation) into food, food stuffs, feed, or drink.

Some embodiments of the invention include methods for screening molecules for translocation. As used herein, the term "leakage" indicates the crossing of non-water components across the lipid bilayer, such as that observed with pore-formation in a lipid bilayer; leakage includes movement of non-water components from the intra-liposomal solution to the extra-liposomal solution and movement of non-water components from the extra-liposomal solution to the intra-liposomal solution. As used herein, the term "translocation" indicates crossing a lipid bilayer by a screening molecule with little, if any, crossing of other non-water components across the lipid bilayer (e.g., less than about 20% leakage compared to solubilized bilayer, less than about 15% leakage compared to solubilized bilayer, less than about 10% leakage compared to solubilized bilayer, or less than about 5% leakage compared to solubilized bilayer). The method for screening can include a determination of leakage from a liposome and a determination of crossing a liposomal lipid bilayer by the screened molecule.

In some embodiments, the method for screening molecules for translocation comprises: (a) contacting a molecule to be screened with a liposomal solution, (b) determining leakage of a liposome and (c) determining crossing a liposomal lipid bilayer by the screened molecule. The intra-liposome solution comprises a first intra-liposome molecule that upon leakage of the liposome can complex (by ionic or covalent bonds or both) with an extra-liposome molecule to provide a first measureable entity; this complexation can occur inside the leaky liposome, outside the leaky liposome, or both. The screening molecule comprises a cleavable moiety that upon contact with an intra-liposome enzyme or the intra-liposomal environment (e.g., changes in pH, oxidation environment, or ionic strength) can cleave the cleavable moiety to provide a second measurable entity. The extra-liposome solution can comprise an extra-liposome inhibitor to the intra-liposome enzyme to prevent cleavage of the cleavable moiety if the liposome leaks. The determination of leakage can be an absolute rate of leakage, a relative rate of leakage (e.g., compared to that of another molecule or a control solution), an absolute amount of leakage, or a relative amount of leakage (e.g., compared to that of another molecule or a control solution). The determination of crossing a liposomal bilayer can be an absolute rate of crossing, a relative rate of crossing (e.g., compared to that of another molecule or a control solution), an absolute extent of crossing, or a relative extent of crossing (e.g., compared to that of another molecule or a control solution).

The amount of the first measurable entity can be determined by any suitable method, such as (a) by spectroscopic methods (e.g., fluorescence, absorption, phosphorescence, or NMR) or (b) by radioactive decay (e.g., by liquid scintillation counting) of a radiolabeled (e.g., by $^3$H, $^{14}$C or $^{35}$S) first measureable entity. The amount of the second measurable entity can be determined by any suitable method, such as spectroscopic methods (e.g., fluorescence, absorption, phosphorescence, or NMR) or by radioactive decay (e.g., by liquid scintillation counting) of a radiolabeled (e.g., by $^3$H, $^{14}$C or $^{35}$S) second measureable entity.

The cleavable moiety can include but is not limited to a dye (e.g., TAMRA or AMC) or a radiolabeled moiety. The cleavable moiety can be cleaved using an enzyme. The cleavable moiety can also be cleaved as a result of a difference in the environment of the intra-liposome solution and the environment of the extra-liposome solution; such differences can include, but are not limited to, differences in pH, oxidation (e.g., exposure of a disulfide bond in a oxidative extra-liposome environment which could then be cleaved in a reductive intra-liposome environment), an ion concentration, or ionic strength.

The intra-liposome enzyme can be any enzyme that can be used to cleave the cleavable moiety, such as a protease. Some examples of proteases include, serine proteases (such as, but not limited to, chymotrypsin, trypsin, elastase, and subtilisin), threonine proteases, cysteine proteases (such as, but not limited to, actinidain, bromelain, calpains, caspases, cathepsins, mir1-CP, and papain), aspartate proteases (such as, but not limited to, HIV-1 protease, chymosin, cathepsin D, pepsin, and plasmepsin), metalloproteases (such as but not limited to, metalloexopeptidases and metalloendopeptidases), and glutamic acid proteases.

The extra-liposome inhibitor can be any molecule that inhibits the intra-liposome enzyme, including, for example, serine proteases and peptidase inhibitors, such as α 1-antitrypsin, complement 1-inhibitor, antithrombin, α 1-antichymotrypsin, plasminogen activator inhibitor 1, and neuroserpin. The extra-liposome inhibitors also include, but are not limited to, inhibitors of proteases mentioned herein.

In some embodiments, the determination of leakage can be performed by measuring the fluorescence of the first measurable entity, including, but not limited to Tb$^{3+}$/DPA (dipiccolinic acid), ANTS/DPX (ANTS is 8-aminonaphthalene-1,3,6-trisulfonic acid and DPX is p-xylene-bis-pyridinium bromide), a labeled dextran of 3,000 molecular weight, and a labeled dextran of 40,000 molecular weight. Tb$^{3+}$ leakage can be measured by the increase in fluorescence upon formation of the complex Tb$^{3+}$/DPA; excitation and emission wavelengths of 270 and 490 nm, respectively, can be used. The ANTS/DPX assay can be performed by measuring leakage by the relief of quenching of ANTS by co-encapsulated DPX; excitation and emission wavelengths of 350 and 510 nm, respectively, can be used. Fluorescein-dextran leakage can be measured by relief of fluorescein self-quenching; excitation and emission wavelengths of 490 and 520 nm, respectively, can be used. Complete release of probes (corresponding to 100% leakage) can be determined by solubilizing the liposome, such as with Triton-X.

The liposomes can be made from lipids, such as phospholipids, including but not limited to palmitoyloleoylphostadidylcholine, palmitoyloleoyl phostadidylglycerol, phosphatidylethanolamine, dioleoylphosphatidylethanolamine, and phosphatidylcholine. Liposomes bilayers can also include other components, such as, but not limited to, fatty acids, triacylglycerols, glycerophospholipids, spingolipids, and cholesterol. The amount of any one component in the liposome can be any suitable amount, such as at least about 1%, at least about 5%, at least about 10%, at least about 25%, at least about 50%, at least about 75%, no more than 10%, no more than 25%, no more than 50%, no more than about 75%, no more than about 90%, or no more than about 95%.

The diameter of the liposomes can be any suitable diameter, such as, at least about 5 nm, at least about 10 nm, at least about 25 nm, at least about 50 nm, at least about 750 nm, at least about 100 nm, at least about 250 nm, at least about 500 nm, no more than about 3000 nm, no more than about 1000 nm, or no more than about 500 nm.

The liposomes can be designed to reflect a certain cell or organelle type by, for example, adjusting the size of the liposome, the lipid composition of the liposome bilayer, pH of the intra-liposome environment, oxidative environment of the intra-liposome environment, an ion concentration of the intra-liposome environment, or ionic strength of the intra-liposome environment.

The compound to lipid ratio can be any suitable ratio, such as, about 1:1000, about 1:750, about 1:500, about 1:300, or about 1:150. The compound concentration can any suitable concentration, such as be about 0.1 µM, about 0.5 µM, about 1.0 µM, about 2.5 µM, about 5.0 µM, about 7.5 µM, about, 10 µM, or about 15 µM.

The determination of leakage from a liposome and the determination of crossing a liposomal lipid bilayer can be done in the same sample or in different samples. In some embodiments, the determination of leakage from a liposome and the determination of crossing a liposomal lipid bilayer can be done any suitable time, such as, simultaneously, within about 5 seconds, within about 30 seconds, within about 1 minute, within about 10 minutes, within about 30 minutes, within about 1 hour, or within 3 hours.

EXAMPLES

Labeled Peptide Synthesis: Labeled peptides were synthesized with standard FMOC chemistry using manual synthesis. Tentagel NH2 Macrobeads of 50-60 mesh pore size (~0.3 mm diameter dry; 80,000 beads/gram) were used for library synthesis. Active amino groups on the resin were first acylated with an acid-stable, FMOC photocleavable linker, RT1095 from Advanced Chemtech (Louisville, Ky.) followed by the addition of a Gln-Phe-amidomethylcoumarin (AMC) attached by the Gln R-group (FIG. 1). The first round of synthesis occurs at the Gln amino terminus. Combinatorial sites were varied by the split and pool method giving a peptide library in which each bead contains about 1.5 nmole of one library sequence. Sidechain protecting groups were cleaved with trifluoroacetic acid containing ethanedithiol, thioanisole, and anisole.

The library sequence shown in Table 1 contains a 12 L-amino acid framework that may promote translocation in membranes. There are nine combinatorially varied sites at the N-terminus of the library sequence.

TABLE 1

| | $A^1$ | $A^2$ | $A^3$ | $A^4$ | $A^5$ | $A^6$ | $A^7$ | $A^8$ | $A^9$ | Gly | Gln | Phe-(AMC) |
|---|---|---|---|---|---|---|---|---|---|---|---|---|
| Cationic | Arg | Arg/Lys | Arg/Lys | Arg | Arg | Arg | Arg/Lys | Arg | Arg | | | |
| Other | Pro | Leu | Ile/Gly | Leu/Tyr | Pro/Leu | Phe/Gln | Pro/Leu | Leu | Leu | | | |

Labeled peptides synthesized in bulk were purified by reverse phase HPLC. Microsequencing, HPLC, and mass spectrometry were routinely used to verify peptide sequences.

Secondary structure: Secondary structure was determined in a JASCO 810 circular dichroism spectrometer at room temperature.

High throughput screening: For high throughput screening, 100 mM lipid bilayer vesicles were prepared by extrusion in the presence of 50 mM $Tb^{3+}$/citrate and 10 mg/mL chymotrypsin. The external $Tb^{3+}$/citrate and chymotrypsin were removed by gel filtration. To make the screening solution, 50 µM dipicolinic acid (DPA) and 1 µM α 1-antitrypsin were added to the external medium. The lipid composition was about 90% palmitoyloleoylphostadidylcholine (POPC) and about 10% palmitoyloleoyl phostadidylglycerol (POPG).

Figure 2:
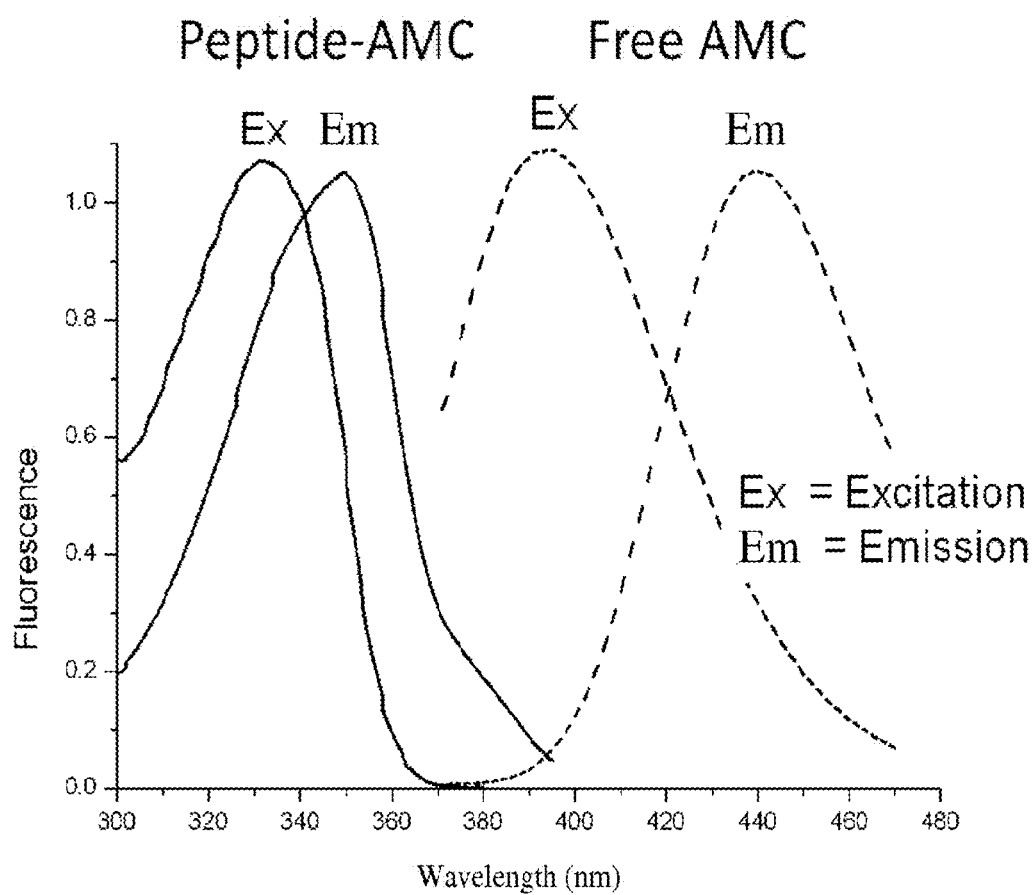
FIG. 2. The spectra of AMC released from the peptide are red-shifted compared to that of the AMC attached to the peptide.
Figure 3:
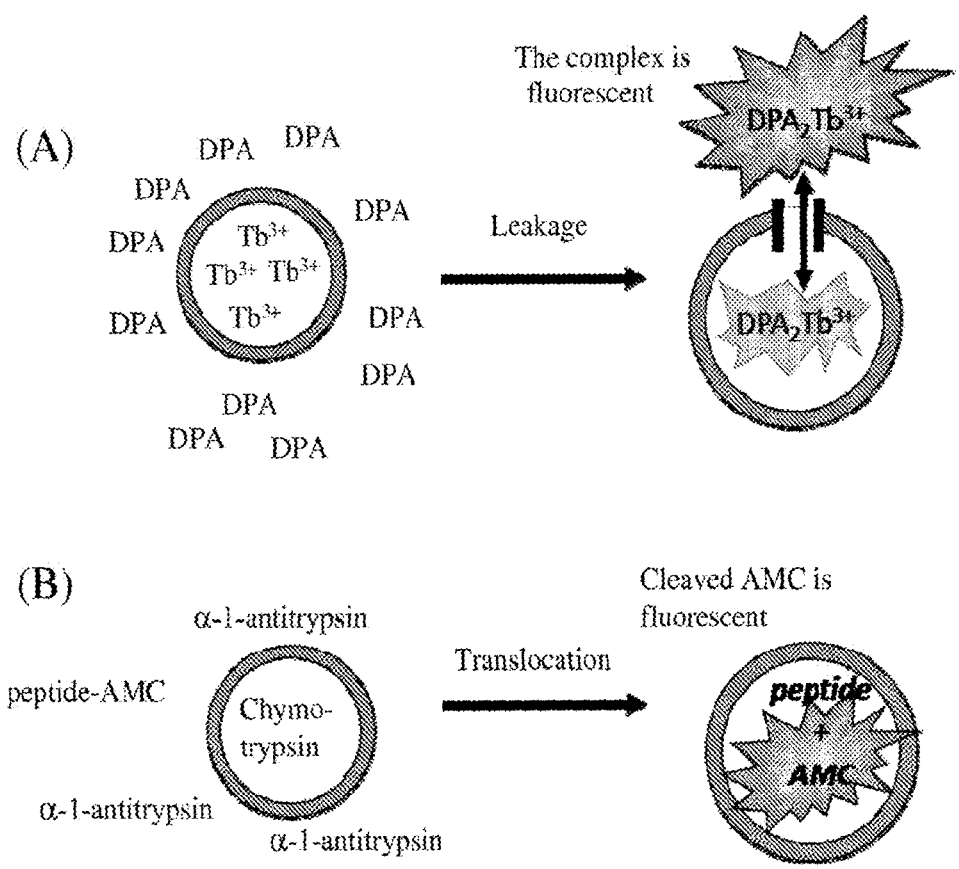
FIG. 3. (A) Peptides that cause leakage result in the $Tb^{3+}$/DPA complex. (B) Peptides that translocate across the bilayer are exposed to the entrapped chymotrypsin, which results in the hydrolysis of the peptide bond contributed by the carboxy group of phenylalanine, freeing the AMC.

The combinatorial labeled peptide library was screened to identify and measure properties of translocation and leakage (e.g., pore-formation). Beads from the synthesis were exposed to longwave UV to cleave the peptide from the resin. The reaction added an amine group to the labeled peptide at the site of cleavage, yielding a Gln residue. Beads were then separated into individual wells of a multiwell plate and the peptides were extracted into 5 µl of dry dimethylsulfoxide overnight. This cleaved approximately 0.75 nmol of labeled peptide from each bead, about half of the total labeled peptide on the bead. A chymotrypsin cleavage site was incorporated into the labeled peptides' design (FIG. 1) and when hydrolysis occurs the AMC fluorophore is released. The spectra of the free AMC fluorophore is red-shifted as compared to that of the peptide-AMC conjugate (FIG. 2). When a labeled peptide translocates, the chymotrypsin inside the vesicle catalyzes the hydrolysis of the peptide bond contributed by the AMC moiety (FIG. 3B). Translocation was monitored by the rate of accumulation of free AMC. In the case of leakage, interaction of the lanthanide metal terbium III ($Tb^{3+}$) with the aromatic chelator dipiccolinic acid (DPA) creates a complex that is fluorescent at low µM concentrations (FIG. 3A). By entrapping $Tb^{3+}$ and chymotrypsin inside the liposomes and then adding dipiccolinic acid and a chymotrypsin inhibitor to the external medium, a visual reporter system for translocation with and without membrane leakage was created that can detect as little as 5 pmol of labeled peptide.

To screen for solubility, the labeled peptide DMSO solution was diluted and incubated for 30 minutes before adding the screening solution. Free-AMC fluorescence was monitored at 450 nm emission (350 nm excitation) for 30 minutes and then the wells were read at 460 nm emission (280 nm excitation) for $Tb^{3+}$/DPA complex formation. Wells with the highest free AMC accumulation and/or $Tb^{3+}$/DPA fluorescence were sent to the Michigan State University Protein Core Facility for sequencing.

Figure 4:
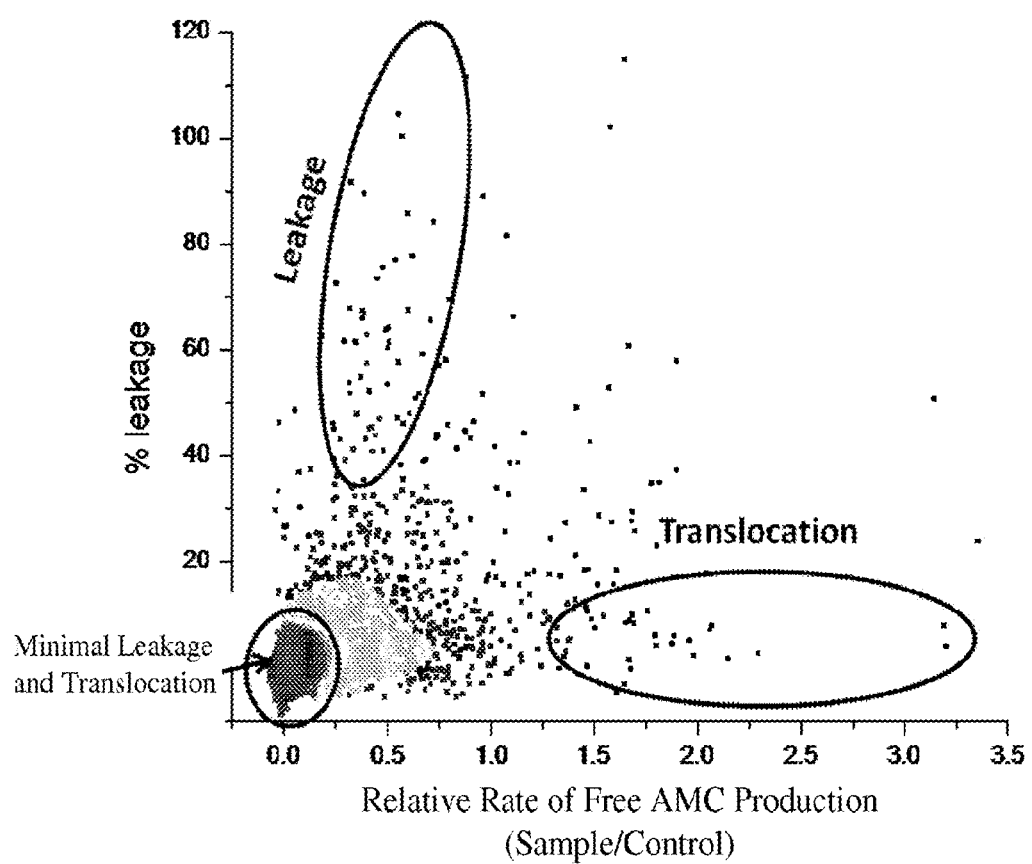
FIG. 4. The distribution of % leakage and relative rate of free AMC production among peptides screened.

The screen was performed at a labeled peptide to lipid ratio of 1:300. A 1:300 labeled peptide:lipid ratio resulted in less than 0.1% of sequences producing a response above minimal leakage and translocation (FIG. 4). In FIG. 4, the oval labeled "Leakage" indicates labeled peptides that show mostly leakage with a minimum of the relative rate of free AMC production. The oval labeled "Translocation" indicates labeled peptides that show a higher relative rate of free AMC production with a minimum of leakage. Roughly 24,000 beads were screened at 1:300 labeled peptide:lipid, a sequence coverage space of 90%. The labeled peptides indicating the highest translocation and highest % leakage were identified by Edman sequencing from the beads.

TABLE 2

| Sequence of Labeled Peptide | % Leakage | Relative Rate of Free AMC Production |
|---|---|---|
| SEQ ID NO: 01 | 24 | 3.4 |
| SEQ ID NO: 02 | −3.0 | 1.6 |
| SEQ ID NO: 03 | 1.7 | 2.1 |
| SEQ ID NO: 04 | 2.8 | 2.3 |

TABLE 2-continued

| Sequence of Labeled Peptide | % Leakage | Relative Rate of Free AMC Production |
|---|---|---|
| SEQ ID NO: 05 | 6.0 | 1.9 |
| SEQ ID NO: 06 | 7.2 | 2.1 |
| SEQ ID NO: 07 | −4.5 | 1.6 |

TABLE 2-continued

| Sequence of Labeled Peptide | % Leakage | Relative Rate of Free AMC Production |
|---|---|---|
| SEQ ID NO: 08 | 5.0 | 2.1 |
| SEQ ID NO: 09 | −0.2 | 1.7 |
| SEQ ID NO: 10 | 26 | 2.3 |
| SEQ ID NO: 11 | 5.2 | 2.0 |
| SEQ ID NO: 12 | 1.6 | 1.7 |
| SEQ ID NO: 13 | 86 | 0.6 |
| SEQ ID NO: 14 | 82 | 1.1 |
| SEQ ID NO: 15 | 105 | 0.0 |
| SEQ ID NO: 16 | 89 | 1.0 |
| SEQ ID NO: 17 | 115 | 1.6 |
| SEQ ID NO: 18 | 92 | 0.3 |
| SEQ ID NO: 19 | 102 | 1.6 |
| SEQ ID NO: 20 | 90 | 0.4 |
| SEQ ID NO: 21 | 84 | 0.7 |

Table 2 shows percent leakage and AMC cleavage rate for labeled peptides selected from the combinatorial library. Free-AMC fluorescence was monitored at 450 nm emission (350 nm excitation) for 30 minutes and then the wells were read at 460 nm emission (280 nm excitation) for $Tb^{3+}$/DPA complex formation. Percent leakage is the % of $Tb^{3+}$ released from lipid vesicles after 60 minutes, compared to a Triton-X 100 detergent-solubilized control (100% leakage). The Relative Rate of Free AMC Production is the rate of free AMC production of the labeled peptide divided by the rate of free AMC production of labeled peptide exposed to a solution that (a) does not comprise the inhibitor, (b) does not comprise liposomes, and (c) comprises a concentration of chymotrypsin that is equal to the concentration of chymotrypsin in the liposome solution (i.e., the amount of chymotrypsin divided by the liposome solution volume, not the intra-liposome solution volume). Free AMC was determined in real time by monitoring the fluorescence of free AMC after vesicle addition using a BioTek Synergy II fluorescence plate reader. The labeled peptides listed above are among the points shown in FIG. 4. The two assays were performed on the same samples.

The labeled peptides in Table 2 show an even distribution of translocating peptides with a lesser degree of leakage and leakage-producing peptides with a lesser degree of translocation.

Leu, Ile, Phe, and Pro occupy a majority of the combinatorial sites in the Table 2 labeled peptides, and show an overabundance ($p<10^{-6}$). These labeled peptides have an average net positive charge of three, provided by arginine, lysine, and the amino terminus. Without being limited by any particular theory, it may be that sometimes cationic residues can have a role in membrane interaction, a first step in translocation and leakage (e.g., pore-formation). Proline is underrepresented (p=0.0245) in the labeled peptide library. Within the framework sequence of this library, there are two sequence motifs distinguishing the translocating labeled peptides from the leakage-producing peptides.

TABLE 3

| | $A^2$ | $A^3$ | $A^4$ | $A^5$ | $A^6$ | $A^7$ | $A^8$ | $A^9$ |
|---|---|---|---|---|---|---|---|---|
| Translocating | Leu 0.02[a] | Ile 0.004[a] | | Leu 0.005[a] | | Leu 0.001[a] | Leu | Arg <10[−6][c] |
| Leakage | | | Leu 0.01[a] | Leu 0.33[a] | Phe 0.049[b] | Leu 0.001[a] | Leu 0.004[a] | Leu <10[−6][c] |

[a] overabundance;
[b] underabundance;
[c] statistic reflects motif of the three amino acids $O^7$, $O^8$, and $O^9$.

Table 3 shows that the translocating labeled peptides have an overabundance of amino acids Leu and Ile at positions two, three, five, and seven. Table 3 also shows that the leakage-producing labeled peptides have an overabundance of Leu at position four, five, seven, and eight. A distinct motif at positions seven through nine further differentiates the translocating labeled peptides from the leakage-producing labeled peptides, Leu-Leu-Arg ($p<10^{-6}$) and Leu-Leu-Leu ($p<10^{-6}$), respectively. Without being bound by any particular theory, it may be possible that Pro and hydrophobic residues (e.g., Leu, Ile, and Phe) can contribute to increased levels of translocation or leakage. Without being bound by any particular theory, Pro and hydrophobic residues located in certain absolute positions or positions relative to one another may also contribute to increased levels of translocation and leakage.

The translocating labeled peptides from the library have an underabundance of lysine whereas the leakage-producing labeled peptides have an occurrence of lysine within what is expected under random insertion. Without being limited by any particular theory, this suggests arginine residues may favor translocation over leakage. Translocating labeled peptides also have an additional charge on average with a large standard deviation. The motif of the leakage-producing labeled peptides includes an underrepresentation of phenylalanine at position six. Without being bound by any particular theory, as the cationic arginine is no more prevalent than the polar glutamine at this position, solubility of the overall labeled peptide may be a selecting factor, rather than the membrane activity of the specific residue.

To confirm the consistency of the assay, two labeled peptides, one positive for translocation with minimal leakage and one positive for leakage with minimal translocation, were synthesized by the same method as with the library, yielding a C-terminal AMC fluorophore. In purified form, the translocating labeled peptide caused detectible free-AMC accumulation with minimal leakage and the positive leakage-producing labeled peptide caused detectible leakage with translocation at 1:300 labeled peptide:lipid. A pool of 100 library labeled peptides did not result in labeled peptide digestion by the encapsulated chymotrypsin or cause substantial leakage, further distinguishing the selected labeled peptides as membrane active.

For further study, the seven L-amino-acid-isomer peptides in Table 4 (below) were synthesized and purified. To study the secondary structure of the peptides, unlabeled cysteine was alkylated to prevent disulfide formation. In solution, these peptides show up to about 50% beta sheet mixed with mostly random coil structure, as measured by circular dichroism spectroscopy. When bound to membranes the peptide secondary structure appears to increase. For example, some of the peptides show 50-75% beta sheet structure, while other peptides show the presence of up to 25% alpha helix structure. No correlation between secondary structure and activity was found in this study. And this study did not find a structure among the membrane active peptides as a whole or when subdivided into translocating and leakage-producing peptides. Without being bound by any particular theory, these results may be consistent with some theories that predict that the translocation or leakage-producing properties of peptides are attributable to primary structure.

Laser Scanning Confocal Fluorescence Microscopy: Some translocating peptides were synthesized and labeled with the fluorescent dye TAMRA on either their amino terminus (N-labeled) or on a C-terminal cysteine residue (C-labeled). Live Chinese Hamster Ovary (CHO) cells were used to assess the ability of the labeled peptides to translocate across living cell membrane into the cells without causing toxicity.

TABLE 4

| Peptides | |
| --- | --- |
| C-terminal cysteine label | N-terminal label |
| SEQ ID NO: 04 | |
| SEQ ID NO: 04 synthesized using all D-amino acids | |
| SEQ ID NO: 10 | SEQ ID NO: 10 |
| SEQ ID NO: 03 | |
| SEQ ID NO: 15 | |
| SEQ ID NO: 18 | SEQ ID NO: 18 |

In Table 4, peptides were labeled with the dye moiety Tetramethyl-6-Carboxyrhodamine ("TAMRA") on a C-terminal cysteine (left column) or on the amino terminus (right column). TAMRA is a polar molecule with a molecular weight of 430.5. All of these labeled peptides were tested for their ability to penetrate the plasma membranes of living cells.

Figure 5:
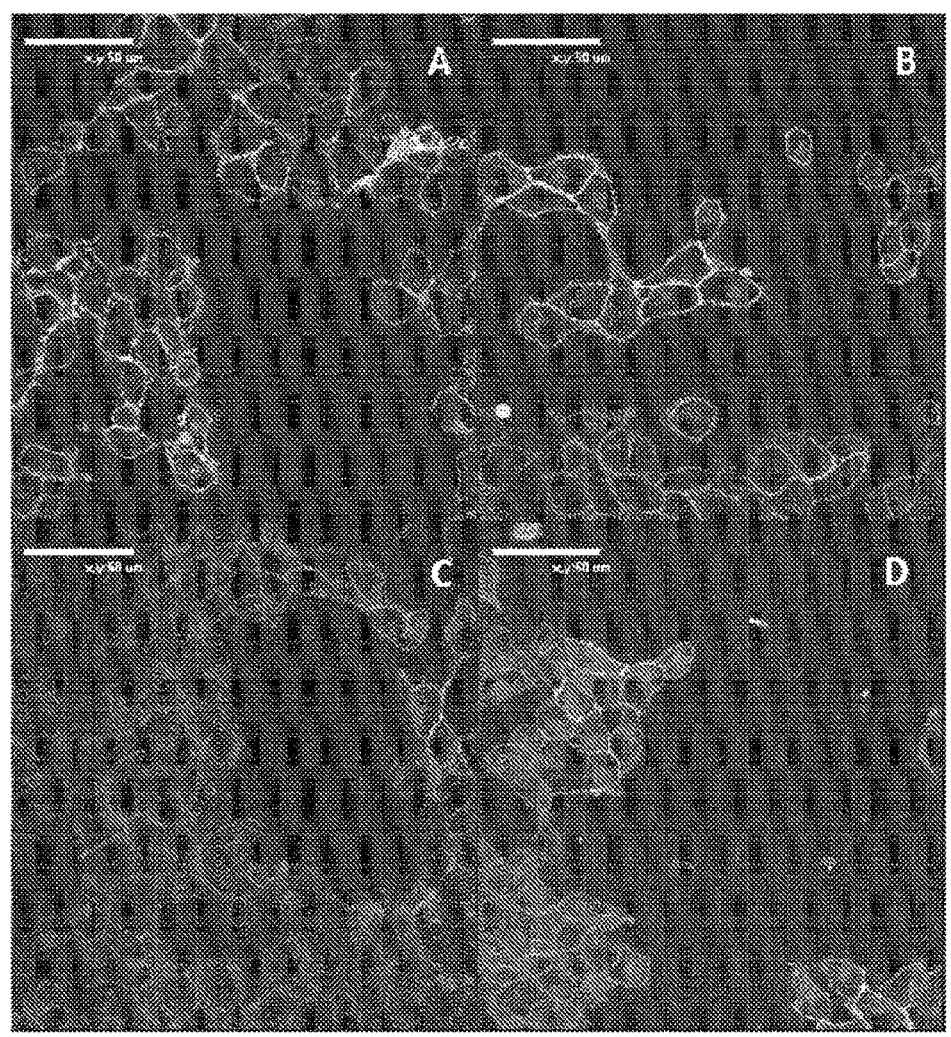
FIG. 5. Representative scanning confocal fluorescence microscopy (CFM) images of translocation of a compound comprising SEQ ID NO:10 as a function of peptide concentration.

FIG. 5 shows representative scanning confocal fluorescence microscopy (CFM) images of translocation of the labeled peptide with SEQ ID NO:10 as a function of labeled peptide concentration. CHO cells were incubated with peptide that was labeled on a C-terminal cysteine residue with the red fluorescent dye TAMRA. Cells and labeled peptide were incubated for 10 minutes in minimal media at 37° C. Cells were then washed to remove labeled peptide from the solution. The minimal media was replaced and 1 μM NBD (7-nitrobenz-2-oxa-1,3-diazol-4-yl) labeled lyso-phosphatidylthanolamine was added to the cells to label the plasma membrane. Labeled peptide concentrations for the panels are: A) 0 μM, B) 2 μM, C) 5 μM, and D) 10 μM. The scale bar represents 50 μm.

The data in FIG. 5 above are representative of the Table 4 labeled peptides. The TAMRA dye, a polar cargo moiety, was carried into the cells by the labeled peptides whether TAMRA was attached at the C-terminus or at the N-terminus of the labeled peptides (as detailed in Table 5). This together with the results of the AMC experiments of the high throughput assays suggest that translocation peptides (e.g., those sequences in Table 4) can deliver diverse cargo (e.g., cargo with various molecular weights, various polarities, or various hydrophobicities) into cells.

Figure 6:
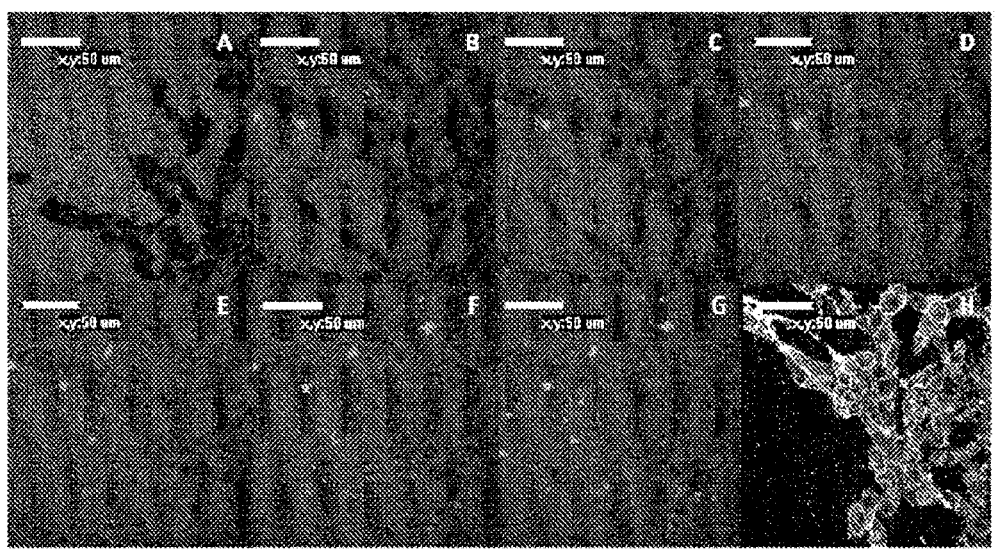
FIG. 6. Representative CFM images monitoring the translocation of a compound comprising SEQ ID NO. 04 (with all D-amino acids for the chiral amino acids) in 10 minute intervals.

Panels A-G of FIG. 6 show representative CFM images monitoring the translocation of a labeled peptide with SEQ ID NO. 04 (synthesized with all D-amino acids for the chiral amino acids) in 10 minute intervals. CHO cells were incubated with the TAMRA-labeled peptide in minimal media and monitored over time at 25° C. without washing. The incubation times for the panels are: A) 5 min., B) 15 min., C) 25 min., D) 35 min., E) 45 min., F) 55 min., and G) 65 min. Panel H shows cells washed after being incubated for 65 minutes and then labeled with 1 μM NBD-labeled lyso-phosphatidylthanolamine. The scale bar represents 50 μm.

In this experiment, the externally added labeled peptide has not been washed away so the solution itself is fluorescent due to added TAMRA-labeled peptide. The black silhouettes in Panel A show the location of cells; before labeled-peptide entry, there is no fluorescence inside the cells. The disappearance of the silhouettes with time indicates that the labeled peptide is transporting the TAMRA moiety into the cells. The shape and coherence of the cells in panel H indicates that toxicity is minimal even after more than an hour of incubation with labeled peptide. Cell penetration occurs within a few minutes and the half-time for cell entry is 20-30 minutes.

TABLE 5

| Labeled Peptide Sequence | Concentration Range Tested | Temperature | Cell Penetrating Half-time | Cell Toxicity (% of cells) |
| --- | --- | --- | --- | --- |
| SEQ ID NO: 04 (C-labeled) | 1.7-10 μM | 37° C. | 20 min. | <5% |
| SEQ ID NO: 04 (D-amino acids) (C-labeled) | 1.7-10 μM | 37° C. | 20 min. | <5% |
| SEQ ID NO: 10 (C-labeled) | 1.7-10 μM | 25° C. | 15 min. | <5% |
| SEQ ID NO: 03 (C-labeled) | 1.7-5 μM | 37° C. | <30 min. | <5% |
| SEQ ID NO: 15 (C-labeled) | 1.7-5 μM | 37° C. | <30 min. | <5% |
| SEQ ID NO: 18 (C-labeled) | 1.7-5 μM | 37° C. | <30 min. | <5% |
| SEQ ID NO: 10 (N-labeled) | 1.7-10 μM | 25° C. | 15 min. | <5% (1-5 μM) 8% (10 μM) |
| SEQ ID NO: 18 (N-labeled) | 1.7-5 μM | 25° C. | <30 min. | <5% |

Table 5 is a summary of cell penetration data from confocal fluorescence microscopy. All labeled peptides tested are able to translocate across living cell membranes and carry the large polar dye molecule TAMRA with them into the cell. Cell penetration was assessed by measuring TAMRA intensity inside CHO cells during incubation with the peptides in Table 4 and comparing intensity inside the cells with the external solution. Incubations were done at either 25° C. or 37° C., at concentrations listed. The half-times for penetration were determined, as shown in Table 5; the half-times have standard deviations of ±10 min. Based on final intensities inside the cells, all labeled peptides tested have similar cell penetrating activity at concentrations tested and at the temperatures tested. Toxicity was determined using the same conditions (e.g., solution and temperature) and concentrations as the cell penetration experiments. Toxicity was assessed by imaging at least 100 cells and counting cells with altered cell morphology, loss of confluence, or loss of adherence to substrate. In some experiments, the non-membrane permeable DNA dye SYTOX green was used to assess membrane integrity. In most cases, no measurable increase in toxicity or membrane integrity over control samples was detectable; this is indicated by the <5% in Table 5.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as a basis for the claims and as a representative basis for teaching one skilled in the art to employ the present invention in any appropriate manner.

What is claimed is:

1. A compound selected from Formula (I)

$$A^1\text{-}A^2\text{-}A^3\text{-}A^4\text{-}A^5\text{-}A^6\text{-}A^7\text{-}A^8\text{-}A^9\text{-}A^{10}\text{-}A^{11}\text{-}A^{12} \qquad (I),$$

Where $A^1$ is selected from the group consisting of L-Arg, D-Arg, L-Pro, and D-Pro;

$A^2$ is selected from the group consisting of L-Arg, D-Arg, L-Lys, D-Lys, L-Leu, and D-Leu;

$A^3$ is selected from the group consisting of L-Arg, D-Arg, L-Lys, D-Lys, L-Ile, D-Ile, and Gly;

$A^4$ is selected from the group consisting of L-Arg, D-Arg, L-Leu, D-Leu, L-Tyr, and D-Tyr;

$A^5$ is selected from the group consisting of L-Arg, D-Arg, L-Pro, D-Pro, L-Leu, and D-Leu;

$A^6$ is selected from the group consisting of L-Arg, D-Arg, L-Phe, D-Phe, L-Gln, and D-Gln;

$A^7$ is selected from the group consisting of L-Arg, D-Arg, L-Lys, D-Lys, L-Pro, D-Pro, L-Leu, and D-Leu;

$A^8$ is selected from the group consisting of L-Arg, D-Arg, L-Leu, and D-Leu;

$A^9$ is selected from the group consisting of L-Arg, D-Arg, L-Leu, and D-Leu;

$A^{10}$ is Gly;

$A^{11}$ is selected from the group consisting of L-Gln and D-Gln; and $A^{12}$ is selected from the group consisting of L-Phe and D-Phe.

2. The compound of claim 1, wherein all of the chiral amino acids in claim 1 are L-amino acids.

3. The compound of claim 1, wherein all of the chiral amino acids in claim 1 are D-amino acids.

4. The compound of claim 1, wherein $A^1$ is selected from the group consisting of L-Pro and D-Pro;

$A^2$ is selected from the group consisting of L-Leu and D-Leu;

$A^3$ is selected from the group consisting of L-Ile, D-Ile, and Gly; and $A^4$ is selected from the group consisting of L-Leu, D-Leu, L-Tyr, and D-Tyr.

5. The compound of claim 1, wherein $A^5$ is selected from the group consisting of L-Leu and D-Leu;

$A^6$ is selected from the group consisting of L-Arg and D-Arg;

$A^7$ is selected from the group consisting of L-Leu and D-Leu;

$A^8$ is selected from the group consisting of L-Leu and D-Leu; and $A^9$ is selected from the group consisting of L-Arg and D-Arg.

6. The compound of claim 1, wherein the compound of claim 1 has a net charge of +2, +3, +4, or +5.

7. The compound of claim 1, wherein $A^7$ is L-Leu or D-Leu; $A^8$ is L-Leu or D-Leu; and $A^9$ is L-Leu or D-Leu.

8. The compound of claim 1, wherein the sum of D-Lys plus L-Lys is less than the sum of D-Arg plus L-Arg.

9. The compound of claim 1, wherein the compound of claim 1 consists of only L-amino acids for the chiral amino acids and is selected from the group consisting of

```
                                        (SEQ ID NO: 1)
Arg-Leu-Ile-Tyr-Leu-Arg-Leu-Leu-Arg-Gly-Gln-Phe;

(SEQ ID NO: 2)
Arg-Lys-Ile-Leu-Leu-Arg-Leu-Leu-Arg-Gly-Gln-Phe;

(SEQ ID NO: 3)
Pro-Leu-Ile-Leu-Leu-Arg-Leu-Leu-Arg-Gly-Gln-Phe;

(SEQ ID NO: 4)
Pro-Leu-Ile-Tyr-Leu-Arg-Leu-Leu-Arg-Gly-Gln-Phe;

(SEQ ID NO: 5)
Pro-Leu-Gly-Tyr-Leu-Phe-Leu-Leu-Arg-Gly-Gln-Phe;

(SEQ ID NO: 6)
Arg-Leu-Ile-Leu-Leu-Phe-Arg-Leu-Arg-Gly-Gln-Phe;

(SEQ ID NO: 7)
Pro-Leu-Arg-Leu-Arg-Phe-Leu-Leu-Arg-Gly-Gln-Phe;

(SEQ ID NO: 8)
Arg-Leu-Ile-Arg-Leu-Phe-Leu-Leu-Arg-Gly-Gln-Phe;

(SEQ ID NO: 9)
Pro-Leu-Ile-Tyr-Pro-Phe-Leu-Arg-Leu-Gly-Gln-Phe;

(SEQ ID NO: 10)
Arg-Arg-Ile-Leu-Leu-Gln-Leu-Leu-Arg-Gly-Gln-Phe;

(SEQ ID NO: 11)
Pro-Leu-Arg-Leu-Arg-Leu-Leu-Arg-Gly-Gln-Phe;
```

```
                                              (SEQ ID NO: 12)
Pro-Lys-Ile-Leu-Leu-Phe-Lys-Leu-Leu-Gly-Gln-Phe;

(SEQ ID NO: 13)
Pro-Arg-Lys-Leu-Leu-Gln-Leu-Leu-Leu-Gly-Gln-Phe;

(SEQ ID NO: 14)
Pro-Arg-Ile-Tyr-Leu-Arg-Leu-Leu-Leu-Gly-Gln-Phe;

(SEQ ID NO: 15)
Arg-Arg-Ile-Leu-Leu-Gln-Leu-Leu-Leu-Gly-Gln-Phe;

(SEQ ID NO: 16)
Pro-Arg-Ile-Leu-Leu-Arg-Leu-Leu-Leu-Gly-Gln-Phe;

(SEQ ID NO: 17)
Arg-Leu-Ile-Leu-Arg-Gln-Leu-Leu-Arg-Gly-Gln-Phe;

(SEQ ID NO: 18)
Arg-Lys-Gly-Leu-Leu-Gln-Leu-Leu-Leu-Gly-Gln-Phe;

(SEQ ID NO: 19)
Arg-Leu-Ile-Leu-Arg-Gln-Leu-Leu-Leu-Gly-Gln-Phe;

(SEQ ID NO: 20)
Pro-Lys-Gln-Leu-Leu-Arg-Leu-Leu-Leu-Gly-Gln-Phe;
and (SEQ ID NO: 21)
Arg-Lys-Arg-Leu-Leu-Gln-Leu-Leu-Leu-Gly-Gln-Phe.
```

10. The compound of claim 1, wherein the compound of claim 1 consists of only D-amino acids for the chiral amino acids and is

```
Pro-Leu-Ile-Tyr-Leu-Arg-Leu-Leu-Arg-Gly-Gln-Phe.
```

11. A compound consisting of the compound of claim 1 linked to a solid support by a solid support linker.

12. A compound consisting of the compound of claim 1 linked to a cargo molecule by a cargo linker.

13. The compound of claim 12, wherein the cargo molecule is linked to the N-terminus of the compound of claim 1 or the C-terminus of the compound of claim 1.

14. The compound of claim 12, wherein the cargo linker is selected from the group consisting of a covalent bond, a D-cysteine, an L-cysteine, an alkylated L-cysteine, and an alkylated D-cysteine.

15. The compound of claim 12, wherein the cargo linker is designed to be cleaved when the compound of claim 11 proceeds (a) from an extracellular environment to an intracellular environment, (b) from outside an organelle to inside an organelle, or (c) from an extra-liposomal environment to an intra-liposomal environment.

16. The compound of claim 12, wherein the cargo molecule is selected from the group consisting of a dye molecule, a nanoparticle, a DNA molecule, an RNA molecule, a polypeptide, a drug, and a prodrug.

17. The compound of claim 12, wherein the cargo molecule has a molecular weight of less than about 200,000.

18. The compound of claim 12, wherein the compound of claim 1 has a net charge of +2, +3, +4, or +5.

19. The compound of claim 12, wherein $A^7$ is L-Leu or D-Leu; $A^8$ is L-Leu or D-Leu; and $A^9$ is L-Leu or D-Leu.

20. The compound of claim 12, wherein, in the compound of claim 1, the sum of D-Lys plus L-Lys is less than the sum of D-Arg plus L-Arg.

21. The compound of claim 12, wherein the compound of claim 1 consists of only L-amino acids for the chiral amino acids and is selected from the group consisting of

```
                                              (SEQ ID NO: 1)
Arg-Leu-Ile-Tyr-Leu-Arg-Leu-Leu-Arg-Gly-Gln-Phe;

(SEQ ID NO: 2)
Arg-Lys-Ile-Leu-Leu-Arg-Leu-Leu-Arg-Gly-Gln-Phe;

(SEQ ID NO: 3)
Pro-Leu-Ile-Leu-Leu-Arg-Leu-Leu-Arg-Gly-Gln-Phe;

(SEQ ID NO: 4)
Pro-Leu-Ile-Tyr-Leu-Arg-Leu-Leu-Arg-Gly-Gln-Phe;

(SEQ ID NO: 5)
Pro-Leu-Gly-Tyr-Leu-Phe-Leu-Leu-Arg-Gly-Gln-Phe;

(SEQ ID NO: 6)
Arg-Leu-Ile-Leu-Leu-Phe-Arg-Arg-Leu-Gly-Gln-Phe;

(SEQ ID NO: 7)
Pro-Leu-Arg-Leu-Arg-Phe-Leu-Leu-Arg-Gly-Gln-Phe;

(SEQ ID NO: 8)
Arg-Leu-Ile-Arg-Leu-Phe-Leu-Leu-Arg-Gly-Gln-Phe;

(SEQ ID NO: 9)
Pro-Leu-Ile-Tyr-Pro-Phe-Leu-Arg-Leu-Gly-Gln-Phe;

(SEQ ID NO: 10)
Arg-Arg-Ile-Leu-Leu-Gln-Leu-Leu-Arg-Gly-Gln-Phe;

(SEQ ID NO: 11)
Pro-Leu-Arg-Leu-Arg-Leu-Leu-Arg-Gly-Gln-Phe;

(SEQ ID NO: 12)
Pro-Lys-Ile-Leu-Leu-Phe-Lys-Leu-Leu-Gly-Gln-Phe;

(SEQ ID NO: 13)
Pro-Arg-Lys-Leu-Leu-Gln-Leu-Leu-Leu-Gly-Gln-Phe;

(SEQ ID NO: 14)
Pro-Arg-Ile-Tyr-Leu-Arg-Leu-Leu-Leu-Gly-Gln-Phe;

(SEQ ID NO: 15)
Arg-Arg-Ile-Leu-Leu-Gln-Leu-Leu-Leu-Gly-Gln-Phe;

(SEQ ID NO: 16)
Pro-Arg-Ile-Leu-Leu-Arg-Leu-Leu-Leu-Gly-Gln-Phe;

(SEQ ID NO: 17)
Arg-Leu-Ile-Leu-Arg-Gln-Leu-Leu-Arg-Gly-Gln-Phe;

(SEQ ID NO: 18)
Arg-Lys-Gly-Leu-Leu-Gln-Leu-Leu-Leu-Gly-Gln-Phe;

(SEQ ID NO: 19)
Arg-Leu-Ile-Leu-Arg-Gln-Leu-Leu-Leu-Gly-Gln-Phe;

(SEQ ID NO: 20)
Pro-Lys-Gln-Leu-Leu-Arg-Leu-Leu-Leu-Gly-Gln-Phe;
and (SEQ ID NO: 21)
Arg-Lys-Arg-Leu-Leu-Gln-Leu-Leu-Leu-Gly-Gln-Phe.
```

22. The compound of claim 12, wherein the compound of claim 1 consists of only D-amino acids for the chiral amino acids and is

```
Pro-Leu-Ile-Tyr-Leu-Arg-Leu-Leu-Arg-Gly-Gln-Phe.
```

23. A compound consisting of the compound of claim 12 linked to a solid support by a solid support linker.

24. A method for administering comprising
    administering at least one compound of claim 1 to a cell or liposome.

25. The method of claim 24, wherein the cell is a unicellular organism or is obtained from a multicellular organism.

26. A method for administering comprising
administering at least one compound of claim 12 to a cell or liposome.

27. The method of claim 26, wherein the cell is a unicellular organism or is obtained from a multicellular organism.

28. A method for administering comprising
administering at least one compound of claim 1 to an animal.

29. The method of claim 28, wherein the animal is selected from the group consisting of canine, bovine, porcine, avian, mammalian, and human.

30. A method for administering comprising
administering at least one compound of claim 12 to an animal.

31. The method of claim 30, wherein the animal is selected from the group consisting of canine, bovine, porcine, avian, mammalian, and human.

32. A pharmaceutical composition comprising at least one compound of claim 1.

33. A pharmaceutical composition comprising at least one compound of claim 12.

34. The compound of claim 12, wherein
the cargo molecule is selected from the group consisting of a dye molecule, a nanoparticle, a DNA molecule, an RNA molecule, a polypeptide, a drug, and a prodrug, and
the cargo linker is selected from the group consisting of a covalent bond; a D-cysteine; an L-cysteine; an alkylated L-cysteine; an alkylated D-cysteine; two cysteines, which can be D-, L-, or both, connected by a disulfide bond or by a peptide bond; one alkylated cysteine, which can be D- or L-, connected by a peptide bond to a cysteine, which can be D- or L-; two alkylated cysteines, which can be D-, L-, or both, connected by a peptide bond; and an amino acid sequence that is cleavable by an enzyme.

35. The compound of claim 12, wherein the compound of claim 12 can pass through a lipid bilayer.

* * * * *

```
                        SEQUENCE LISTING

<160> NUMBER OF SEQ ID NOS: 24

<210> SEQ ID NO 1
   <211> LENGTH: 12
   <212> TYPE: PRT
   <213> ORGANISM: artificial sequence
   <220> FEATURE:
   <223> OTHER INFORMATION: Screened compound comprising this amino acid
         sequence

<400> SEQUENCE: 1

Arg Leu Ile Tyr Leu Arg Leu Leu Arg Gly Gln Phe
   1               5                   10

<210> SEQ ID NO 2
   <211> LENGTH: 12
   <212> TYPE: PRT
   <213> ORGANISM: artificial sequence
   <220> FEATURE:
   <223> OTHER INFORMATION: Screened compound comprising this amino acid
         sequence

<400> SEQUENCE: 2

Arg Lys Ile Leu Leu Arg Leu Leu Arg Gly Gln Phe
   1               5                   10

<210> SEQ ID NO 3
   <211> LENGTH: 12
   <212> TYPE: PRT
   <213> ORGANISM: artificial sequence
   <220> FEATURE:
   <223> OTHER INFORMATION: Screened compound comprising this amino acid
         sequence

<400> SEQUENCE: 3

Pro Leu Ile Leu Leu Arg Leu Leu Arg Gly Gln Phe
   1               5                   10

<210> SEQ ID NO 4
   <211> LENGTH: 12
   <212> TYPE: PRT
   <213> ORGANISM: artificial sequence
   <220> FEATURE:
   <223> OTHER INFORMATION: Screened compound comprising this amino acid
         sequence

<400> SEQUENCE: 4

Pro Leu Ile Tyr Leu Arg Leu Leu Arg Gly Gln Phe
   1               5                   10

<210> SEQ ID NO 5
   <211> LENGTH: 12
   <212> TYPE: PRT
   <213> ORGANISM: artificial sequence
   <220> FEATURE:
   <223> OTHER INFORMATION: Screened compound comprising this amino acid
         sequence

<400> SEQUENCE: 5

Pro Leu Gly Tyr Leu Phe Leu Leu Arg Gly Gln Phe
```

```
<210> SEQ ID NO 6
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 6

Arg Leu Ile Leu Leu Phe Arg Arg Leu Gly Gln Phe
1               5                   10

<210> SEQ ID NO 7
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 7

Pro Leu Arg Leu Arg Phe Leu Leu Arg Gly Gln Phe
1               5                   10

<210> SEQ ID NO 8
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 8

Arg Leu Ile Arg Leu Phe Leu Leu Arg Gly Gln Phe
1               5                   10

<210> SEQ ID NO 9
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 9

Pro Leu Ile Tyr Pro Phe Leu Arg Leu Gly Gln Phe
1               5                   10

<210> SEQ ID NO 10
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 10

Arg Arg Ile Leu Leu Gln Leu Leu Arg Gly Gln Phe
1               5                   10

<210> SEQ ID NO 11
<211> LENGTH: 12
<212> TYPE: PRT
<213> ORGANISM: artificial sequence
<220> FEATURE:
<223> OTHER INFORMATION: Screened compound comprising this amino acid
      sequence
```

```
<400> SEQUENCE: 11

Pro Leu Arg Leu Leu Arg Leu Leu Arg Gly Gln Phe
1               5                   10

<210> SEQ ID NO 12
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 12

Pro Lys Ile Leu Leu Phe Lys Leu Leu Gly Gln Phe
1               5                   10

<210> SEQ ID NO 13
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 13

Pro Arg Lys Leu Leu Gln Leu Leu Leu Gly Gln Phe
1               5                   10

<210> SEQ ID NO 14
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 14

Pro Arg Ile Tyr Leu Arg Leu Leu Leu Gly Gln Phe
1               5                   10

<210> SEQ ID NO 15
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 15

Arg Arg Ile Leu Leu Gln Leu Leu Leu Gly Gln Phe
1               5                   10

<210> SEQ ID NO 16
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 16

Pro Arg Ile Leu Leu Arg Leu Leu Leu Gly Gln Phe
1               5                   10

<210> SEQ ID NO 17
<211> LENGTH: 12
<212> TYPE: PRT
```

```
<213> ORGANISM: artificial sequence
<220> FEATURE:
<223> OTHER INFORMATION: Screened compound comprising this amino acid
      sequence

<400> SEQUENCE: 17

Arg Leu Ile Leu Arg Gln Leu Leu Arg Gly Gln Phe
1               5                   10

<210> SEQ ID NO 18
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 18

Arg Lys Gly Leu Leu Gln Leu Leu Leu Gly Gln Phe
1               5                   10

<210> SEQ ID NO 19
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 19

Arg Leu Ile Leu Arg Gln Leu Leu Leu Gly Gln Phe
1               5                   10

<210> SEQ ID NO 20
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 20

Pro Lys Gln Leu Leu Arg Leu Leu Leu Gly Gln Phe
1               5                   10

<210> SEQ ID NO 21
<211> LENGTH: 12
<212> TYPE: PRT
<213> ORGANISM: artificial sequence
<220> FEATURE:
<223> OTHER INFORMATION: Screened compound comprising this amino acid
      sequence

<400> SEQUENCE: 21

Arg Lys Arg Leu Leu Gln Leu Leu Leu Gly Gln Phe
1               5                   10

<210> SEQ ID NO 22
<211> LENGTH: 12
<212> TYPE: PRT
<213> ORGANISM: artificial sequence
<220> FEATURE:
<223> OTHER INFORMATION: Compound comprising this amino acid sequence

<400> SEQUENCE: 22

Arg Lys Lys Arg Arg Gln Arg Arg Arg Gly Gln Phe
1               5                   10
```

```
<210> SEQ ID NO 23
<211> LENGTH: 12
<212> TYPE: PRT
<213> ORGANISM: artificial sequence
<220> FEATURE:
<223> OTHER INFORMATION: Compound comprising this amino acid sequence

<400> SEQUENCE: 23

Arg Arg Arg Arg Arg Arg Arg Arg Arg Gly Gln Phe
1               5                   10

<210> SEQ ID NO 24
<211> LENGTH: 7
<212> TYPE: PRT
<213> ORGANISM: artificial sequence
<220> FEATURE:
<223> OTHER INFORMATION: Compound comprising this amino acid sequence

<400> SEQUENCE: 24

Arg Arg Ile Arg Pro Arg Pro
1               5
```